(12) United States Patent
Jones et al.

(10) Patent No.: US 7,697,141 B2
(45) Date of Patent: Apr. 13, 2010

(54) IN SITU OPTICAL COMPUTATION FLUID ANALYSIS SYSTEM AND METHOD

(75) Inventors: Christopher M. Jones, Missouri City, TX (US); Louis W. Elrod, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 656 days.

(21) Appl. No.: 11/297,282

(22) Filed: Dec. 8, 2005

(65) Prior Publication Data

US 2006/0142955 A1 Jun. 29, 2006

Related U.S. Application Data

(60) Provisional application No. 60/634,703, filed on Dec. 9, 2004.

(51) Int. Cl.
*G01N 21/55* (2006.01)
(52) U.S. Cl. .................................................. 356/445
(58) Field of Classification Search ................. 356/445, 356/326
See application file for complete search history.

(56) References Cited

U.S. PATENT DOCUMENTS

| | | | |
|---|---|---|---|
| 3,717,078 A | | 2/1973 | Ogura |
| 5,223,715 A | * | 6/1993 | Taylor ......................... 250/343 |
| 5,734,098 A | * | 3/1998 | Kraus et al. ................. 73/61.62 |
| 5,991,048 A | * | 11/1999 | Karlson et al. .............. 356/445 |
| 6,176,323 B1 | | 1/2001 | Weirich et al. |
| 6,198,531 B1 | | 3/2001 | Myrick et al. |
| 6,420,708 B2 | * | 7/2002 | Wilks et al. ............. 250/339.07 |
| 6,469,785 B1 | * | 10/2002 | Duveneck et al. ........... 356/244 |
| 6,529,276 B1 | | 3/2003 | Myrick |
| 7,123,844 B2 | * | 10/2006 | Myrick ....................... 398/192 |
| 2003/0056581 A1 | | 3/2003 | Turner et al. |
| 2003/0071988 A1 | | 4/2003 | Smith et al. |
| 2004/0012782 A1 | * | 1/2004 | Mason et al. ............... 356/338 |

(Continued)

FOREIGN PATENT DOCUMENTS

JP 57142546 9/1982

OTHER PUBLICATIONS

Betancourt, Soraya et al., "Analyzing Hydrocarbons in the Borehole", Oilfield Review, Autumn 2003, pp. 54-61.

(Continued)

*Primary Examiner*—Kara E Geisel
(74) *Attorney, Agent, or Firm*—Schwegman, Lundberg & Woessner, P.A.

(57) ABSTRACT

A multivariate optical element (MOE) calculation device is used in an apparatus for determining a property of petroleum in real time flowing in a pipe in petroleum field stream pipes or pipe line. Multiple apparatuses are provided for determining the amount of each of a plurality of properties. An internal reflectance element (IRE) is used to determine the property of the petroleum from a surface of the petroleum flowing in a pipe. A cleaning apparatus is provided to clean the surface of the IRE in the pipe and a turbulence generator is provided in the pipe to insure homogeneity of the petroleum being analyzed prior to analysis. A bellows may be provided the apparatus housing to compensate for pressure differentials between the housing and the flowing petroleum in the pipe. Various embodiments are disclosed.

48 Claims, 11 Drawing Sheets

U.S. PATENT DOCUMENTS

2006/0093523 A1* 5/2006 Norman .................. 422/83

OTHER PUBLICATIONS

Eastwood, DeLyle, et al., Field applications of stand-off sensing using visible/NIR multivariate optical computing, Ground and Air Pollution Monitoring and Remediation, SPIE vol. 4199 (2001), pp. 105-114.

Haibach et al., "On-line Reoptimization of Filter Designs for Multivariate Optical Elements", Applied Optics, vol. 42, No. 10, pp. 1833-1838, Apr. 1, 2003.

Mullins et al., "Gas-Oil Ratio of Live Crude Oils Determined by Near-Infrared Spectroscopy", Optical Methods for Industrial Processes, Proceedings of SPIE vol. 4201 (2001) pp. 73-81.

Myrick et al., "Application of Multivariate Optical Computing to Near-Infrared Imaging", Proceedings of SPIE, vol. 4577, (2002) pp. 148-157.

Myrick, M.L. et al., "Application of multivariate optical computing to simple near-infrared ponit measurements", Instrumentation for Air Polution and Global Atmospheric Monitoring, Proceedings of SPIE vol. 4574 (2002) pp. 208-215.

Myrick, M.L., et al., "A single-element all-optical approach to chemometric prediction", Vibrational Spectroscopy 28 (2002), pp. 73-81.

Myrick, Michael, "Multivariate Optical Elements Simplify Spectroscopy", GSI Lumonics web site, Laser Focus World, 2004.

Nelson, Matthew P. et al., "Multivariate optical computation for predictive spectroscopy", SPIE Vo. 3261, pp. 232-243, 1998.

Soyemi, Olusola et al., "A Simple Optical Computing Device For Chemical Analysis", Proceedings of SPIE Vo. 4284 (2001) pp. 17-28.

Soyemi, O. et al., "Design and Testing of a Multivariate Optical Element: The First Demonstration of Multivariate Optical Computing for Predictive Spectroscopy", Analytical Chemistry, vol. 73, No. 6, Mar. 15, 2001, pp. 1069-1079.

Soyemi, Olusola et al., "Design of angle tolerant multivariate optical elements for chemical imaging", Applied Optics, vol. 41, No. 10, Apr. 1, 2002, pp. 1936-1941.

Soyemi, Olusola et al., "Nonlinear Optimization Algorithm for Multivariate Optical Element Design", Applied Spectroscopy, vol. 56, No. 4, 2002, pp. 477-487.

Soyemi, Olusola, et al., Novel Filter Design Algorithm for Multivariate Optical Computing, Advanced Environmental and Chemical Sensing Technology, Proceedings of SPIE Vo. 4205 (2001), pp. 288-299.

Strausz et al., "About the Colloidal Nature of Asphaltenes and the MW of Covalent Monomeric Units", American Chemical Society, Energy and Fuels 16, No. 4, (2002) (abstract).

Aske, N. et al., "Determination of Saturate, Aromatic, Resin, and Asphitenic (SARA) Components in Crude Oils by Means of Infrared and Near-Infrared Spectroscopy", American Chemical Society, Energy and Fuels 15, No. 5, pp. 134-1312, 2001.

Aske, Narve et al., "Asphaltene Aggregation from Crude Oils and Models Systems Studied by High-Pressure NIR Spectroscopy"Energy and Fuels, American Chemical Society, 16, No. 5, (2002) pp. 1287-1295.

Sastry et al., "Determination of Physiocochemical Properties and Carbon-Type Analysis of Base Oils Using Mid-IR Spectroscopy and Partial Least Squares Regression Analysis", American Chemical Society, Energy and Fuels 12, No. 2, pp. 304-311, (2002).

* cited by examiner

IN SITU OPTICAL COMPUTATION FLUID ANALYSIS SYSTEM AND METHOD

This application claims the benefit of provisional application Ser. No. 60/634,703 filed Dec. 9, 2004 and incorporated by reference herein in its entirety.

This invention relates to optical analysis systems and methods for analyzing fluids, for example, crude petroleum, e.g., flowing in a pipe, or in a crude petroleum well, or being extracted from a well or from or in a reservoir, and in particular, to optical analysis systems for such fluids.

Optical spectroscopy is an analytical technique that derives information about the system being evaluated by the interaction of that system with light in the UV to ir range. The interaction changes the properties of the light, specifically the frequency (color), intensity, polarization, or direction (scattering or refraction).

Spectroscopy has been used in petroleum fields, more commonly referred to as oil fields, extensively to derive information about a chemical or physical system. Schlumberger has used spectroscopy recently as the analytical technique for petroleum rig drilling down hole instruments known as Live Fluid Analyzer Compositional Fluid Analyzer, Optical Fluid Analyzer, and PVT Express. Sperry Sun uses an instrument referred to as the LaserStrat Device to make stratigraphic correlations at an oil rig well site. Intertek Westport Technology Center, assignee of the present application, is field testing a laser spectroscopic device for measuring the isotope content of methane. Many companies use spectroscopy as the principal technique to make fluid (water, gas and oil) and geological chemical and physical measurements at well sites.

Crude petroleum fields can contain numerous reservoirs. A production platform may contain many wells to a number of different reservoirs all coupled to common production tubing. Such systems may include both vertical and horizontal pipes. These pipes form numerous streams that may experience various problems from time to time due to the components or changes in the composition of the components in the fluid and physical changes to the system such as temperature and pressure during the extraction process. In such fields such as the North Sea, well heads on the ocean floor may comprise numerous wells in each head. The wells are interconnected by streams wherein each stream may interconnect with five to ten reservoirs simultaneously, for example. Problems with flow assurances can be costly to such a field operating costs.

Asphaltenes, for example may present one type of problem, are present in the crude petroleum and are in solution in the petroleum stabilized by resins. If the relative resin content decreases, the asphaltenes may precipitate out of the fluid and deposit on the pipe walls, restricting or interrupting flow. It is relative costly to remove such asphalt deposits which require grinding or scraping operations. Robots are used to scrape the pipes and some times if not removed, the deposits may shut down a pipe. It is difficult to sample the oil in such complex streams for properties of the oil at any given time. The asphaltene and resin content needs to be continuously monitored to preclude flow assurance problems before these problems interfere with production. When a problem occurs, it may cost $5-20 million to fix it. At any one time, the well heads may be producing about only 90% capacity due to such problems. Total flow assurance problems for the North Sea may cost upward of $240 million annually. It is estimated that $100 million is spent annually on prevention of problems in the North Sea field. Maintaining flow can add considerably production costs and reduce profits. No major oil producing field is without production problems.

Optical spectroscopy is frequently used to analyze samples in an oil field in an attempt for prevention or problem solving. Optical spectroscopy techniques are costly, slow and cumbersome to implement and frequently require an elevated level of expertise at the wellsite.

Optical spectra are transformed into chemical or physical information relating to the material under examination based on the relationship of the spectra to the chemical or physical information. Interference and matrix effects can mask the relationship and limit the applicability of spectroscopy. In general, natural systems including geological and petroleum systems rarely are sufficiently free of interference and matrix effects without extensive sample preparation. Additionally, optical spectroscopy has limited use in determining physical properties. Either the physical property must have a direct correlation to a chemical property or a model describing a physical property as a function of a number of chemical properties must be well defined.

Spectrometers and associated computers are expensive and comprise the most delicate components of an optical spectroscopy system. Only a few spectrometers are suitable for down hole applications, and are costly to implement.

With respect to petroleum well applications for extracting crude petroleum from the ground, flow assurances of the petroleum can be a costly aspect of normal production operations. Flow assurances problems can be related to wax deposition, asphaltene deposition, foaming, hydrate formations, corrosion, solid particles, reservoir erosion, and scale among others. Asphaltenes are in solution in the petroleum. If asphaltene precipitates out of solution due to change in composition or a change in pressure, it tends to restrict or clog pipelines and is costly to remove. Hydrates formed by methane and water are crystals which also if present may clog pipes. Tubing or casing failure can alter flow or cause other production problems and should be monitored. Aromatics and naphthanates when combined with water somewhat like water combined with soap, can causes formation of foam and/or emulsions and causes flow restriction or interruption. It is important to determine treatment effectiveness of scale, corrosion, wax and asphaltene as well as monitoring sand/chalk loss, all of which can adversely affect production. Monitoring flow assurance issues created by the above described components requires good forecasting and proper feedback.

Avoiding flow assurance issues before they occur will mitigate costly corrective action. In some cases, production of a well from a particular reservoir can be permanently damaged by flow problems making prevention essential to proper reservoir management. In addition to flow assurance, water production can be a difficult problem. As oil is depleted from a unit of a reservoir, the production may yield higher proportions of water. The water reduces total hydrocarbon production and must be disposed of properly. Such water can substantially reduce the economics of a well. Identifying the "watering out" zone to allow it to be shut off is an important part of reservoir management. Reservoir erosion can also adversely affect production by adding particulates to the stream and altering subsurface flow characteristics. Pinpointing the location of reservoir erosion is also a necessary part of reservoir management.

Determining petroleum quality while drilling can impact real-time decisions such as which zones to test among numerous zones in a complex field, and the number and type of samples to take. When fluid samples are acquired, they must be evaluated for contamination, which can render them useless for future analysis. Petroleum quality information can also affect logging decisions, including which logs to take and which zones to log. Sampling and logging can cost millions of dollars and down time for the drilling process. Proper decision making requires proper information. Obtaining proper information with present slow, cumbersome methods is costly and frequently does not deliver the information in time.

Another problem is monitoring well bore pressure. Under balanced drilling presents a new range of problems. As new formations are penetrated by drilling, a risk is run of exceeding the desired pressure differentials. Pressure differentials are currently forecasted by models while drilling, but need high quality information. In addition, during under balanced drilling, the drilling fluid can receive a continuous stream of hydrocarbons from all penetrated zones. This provides the opportunity to characterize the hydrocarbons from the various zones, but the problem is complex because of the mixing of the hydrocarbons.

The present inventors recognize that the properties of petroleum that are of interest for monitoring the quality of the petroleum include, but are not limited to: SARA (saturates, aromatics, resins and asphaltenes), $H_2O$ ion-composition and content, hydrocarbon composition and content, solid particulate content. GOR (gas oil ratio), bubble point, density (API), petroleum formation factor, viscosity, gas phase such as methane, ethane, propane, butane, pentane, oxygen, $H_2S$ and $CO_2$, total stream percentage of water, gas, oil, solid particles, solid types, oil fingerprints, reservoir continuity and oil type, anions, cations, salinity, organics, $CO_2$, $H_2S$, pH, mixing ratios, tracer concentrations and contaminants.

Two regression techniques can minimize matrix and contamination effects noted above. Known spectral analysis systems employs principal component regression (PCR) or partial least squares analysis (PLS) of various petroleum and non-petroleum fluid spectra using spectrometers linked to computers. These techniques can minimize the matrix and contamination effects and more clearly determine the relationship of the spectra to the properties to be measured.

However, as discussed above, natural systems including geological and petroleum systems rarely are conducive to a classic spectral analysis case without extensive sample preparation. Additionally, as noted above, classical spectroscopy has limited use in determining physical properties and can be costly and cumbersome to implement.

The present inventors recognize the existence of a relatively new technology that employs multivariate optical elements (MOE). They importantly recognize that such technology is useful for petroleum field stream and pipeline monitoring for solving the present problems presented by prior art spectroscopic systems now in use in such fields. An MOE is an optical computer that the inventors recognize as having advantageous ruggedness, low cost and accuracy properties well suited for application to analysis in a petroleum drilling field and for petroleum pipeline monitoring in a hostile environment produced at elevated underground temperatures and pressures or in remote and hostile settings.

Such optical computers are typically presently employed for analysis of static fluid samples, in a laboratory for example. See the cited references below. MOE computers are used in systems that employ multivariate regression and may be referred to as optical chips for analog optical computing. In such systems, light is transformed into chemical or physical information through the use of regression techniques. Such filters represent pattern recognition systems which recognize certain spectra patterns using vector regression techniques. The concept of transforming light through the use of regression is dependent upon the fact that matter interacts with specific frequencies of light depending upon the chemical nature to modify the intensity of that light.

Light has a wave and particle dual nature. With respect to the wave aspect, light can be subject to addition and subtraction, overlapping wave peaks can intensify in an additive sense or peaks and valleys can overlap subtracting and canceling one another. With respect to the particle aspect, light can be subject to multiplication and division. Therefore operating on light with interference filters can produce mathematical equivalent operations of addition, subtraction, multiplication and division.

The present inventors recognize that a multivariate optical element (MOE) spectral analysis system can provide a relatively low cost, rugged and accurate system for monitoring petroleum quality for the purpose of optimizing decision making at the well site and efficient management of hydrocarbon production as described above and can be dispersed to a multitude of streams efficiently and effectively at low cost. The problem addressed is analysis of dirty and ill determined compositional dynamic and flowing systems, whereas current use has been limited to static well defined systems in laboratories.

As discussed above, prior art spectroscopy systems are mainly utilized with static samples taken from a well field or pipeline or short term use, e.g., an hour. In one instance, a traditional spectroscopic system was attached to a downhole sampler. Such a system is costly to implement. The spectroscopic system is exposed to extreme conditions of temperature and pressure in an underground pipe, which conditions are detrimental to the computer and spectroscopy instruments of such a system. These instruments require an insulated pressure controlled environment that is attached to the sampler. Because the use is short term, this is a special situation and not widely used due to its complexity and cost.

The inventors are also aware that traditional spectroscopic systems are used in conjunction with monitoring petroleum in a pipeline. These systems are simplistic and can only be used to determine a very limited number of properties of petroleum. There is a significant difference in monitoring a single pipeline as compared to the need for monitoring numerous streams in a petroleum drilling field involving multiple reservoirs and interconnected pipes in a complex field system such as in the North Sea. Traditional spectroscopic instruments are not applicable to such complex situations.

A need is seen by the present inventors for a system and method for monitoring crude petroleum with respect to detecting unacceptable values of one or more of the components of the crude petroleum as discussed above at low cost in real time and automatically. A need is seen for a rugged low cost system that can be widely dispersed into the various streams of a complex petroleum field or used down-hole during the drilling process. Such monitoring is to effect immediate corrective or preventive action or proper decision-making at the time when flow assurance problems are first detected or a drilling decision involving hydrocarbon properties is required. A need is seen for automating such monitoring to more efficiently implement corrective action and also a need for evaluating petroleum problem treatments. The present inventors are not aware of any known low cost rugged spectroscopic system available for monitoring one or more underground streams automatically in real time and that can withstand the temperature and pressure levels required of such monitoring.

U.S. Pat. No. 6,198,531 ('531) to Myrick et al. discloses an optical computation system using MOE filters. An optical filter mechanism (an MOE) receives light from a source and is configured to optically compress data carried by the light into at least one orthogonal component of light. A detector mechanism measures a property of the at least one orthogonal component to measure the data.

Examples include measuring ethylene content and measuring octane of gasoline wherein octane rating is determined by regression analysis. Disclosed is a system that includes a multivariate optical element (MOE) including multiple layers of materials having different refractive indices. The element selectively passes predetermined fractions of light of different wavelengths. Each wavelength is weighted and the materials and the spacings that compose the filter are determined using a variety of approximation methods.

These methods may include determining the inverse Fourier transform (IFT) of the optical transmission spectrum and structuring the filter as the physical representation of the IFT. Another technique for producing such interference filters uses a direct iterative process known as the "needle" method. The method begins with the refractive indices of known materials and an estimate of the filter thickness. Through a computer algorithm, the effect of inserting "needles" of a second material into a first material is estimated. The needles are moved around within the second material, using the interference pattern they create as a guide, until a best approximation of the desired interference pattern is produced. The weightings that the element applies at each wavelength are set to the regression weightings in an equation as described in the patent.

The optical element optically performs a dot product of light and a desired regression vector embodied by the disclosed element which in essence is an optical regression calculation. The intensity of the element light output is directly related to and proportional to the desired information. The patent states that such elements may be produced by a research group including George Dobrolski and Pierre Verly under the National Research Council of Canada. Information regarding the structure of such elements is provided by Applied Optics, Vol. 35, pp. 5484-5492 (1966) AND Vol. 29, pp. 2876-2893 (1990). This patent is incorporated by reference in its entirety herein.

U.S. Pat. No 6,529,276 to Myrick discloses similar subject matter as the '531 patent and includes the identical text and figures of the '531 patent as well as other embodiments and is also incorporated by reference herein in its entirety.

There are numerous published articles on the topic of analyzing crude oil (petroleum). These include:

a. *Gas-Oil Ratio of Live Crude Oils Determined by Near-Infrared Spectroscopy*, Mullins et al., Optical Methods for Industrial Processes, Proceedings of SPIE Vol 4201, 2001, 73-81.

*Asphaltene Aggregation from Crude Oils and Models Systems Studied by High-Pressure NIR Spectroscopy*, Narve Aske et al., Energy and Fuels 16, no. 5, 2002, 1287-1295, American Chemical Society.

*About the Colloidal Nature of Asphaltenes and the MW of Covalent Monomeric Units*, Straysz et al., Energy and Fuels 16, no. 4, 2002, 809-822, American Chemical Society.

*Determination of Saturate, Aromatic, Resin, and Asphltenic (SARA) Components in Crude Oils by Means of Infrared and Near-Infrared Spectroscopy*, Narve Aske et al. Energy and Fuels 15, no. 5, 2001, 13-4-1312, American Chemical Society.

*Determination of Physicochemical Properties and Carbon-Type Analysis of Base Oils Using Mid-IR Spectroscopy and Partial Least Squares Regression Analysis*, Sastry et al., Energy and Fuels 12, no. 2, 2002, 304-311 American Chemical Society.

There are still other numerous articles published on the IR spectroscopy analysis of oils and the like.

An article entitled *Multivariate Optical Elements Simplify Spectroscopy*, Michael Myrick (an inventor in the above noted '276 and '531 patents), GSI Lumonics, web site, Laser Focus World, discloses interference filters with designed spectral properties that perform optical computations for spectroscopic analysis that replaces complex mathematical computations usually performed by a computer on spectroscopic data. Pattern recognition techniques applied to optical spectra of complex mixtures such as gasoline, blood, environmental samples, and so on, are used to detect the presence of specific components measuring their concentrations, or estimating properties that depend on sample chemistry.

Multivariate (multiwavelength) calibration is used infrequently because of the expense and complexity of the spectroscopic tools required. Instruments can be made with the mathematics pattern recognition designed directly into optical interference elements. These elements extract information from light without constructing a spectrum, providing low cost rugged high quality instruments. Optical spectroscopy is effective to fingerprint the composition of matter. However, enough spectroscopic fingerprint is required to be observed to be useful. Multiwavelength optical spectroscopy of complex samples requires multivariate pattern recognition and calibration.

One approach for pattern recognition uses Principal Component Regression (PCR) techniques. Here the magnitude of the pattern in a mixture spectrum is evaluated mathematically by multiplying the intensity of the spectrum at each wavelength by the value of the pattern at the same wavelength, and then summing the result over all wavelengths. The optical spectra and the patterns can be considered as vectors in hyperspace, the actual concentrations of species related to the projection of the spectral vectors onto the pattern vector. These are termed regression vectors.

Multivariate calibration begins with the acquisition of optical spectral in the desired wavelength region for a series of samples with known chemical properties. Calibration methods such as PCR are used to extract a spectral regression pattern that is correlated to a property of interest, but orthogonal to interferences and matrix effects. Prediction of the property in an unknown sample is then carried out by taking the inner product of the regression vector and the optical spectrum of the unknown sample.

Multivariate optical elements (MOE) devices work to make chemical predictions by doing an optical computation equivalent to that computed mathematically by PCR employing traditional spectroscopic instruments. Multivariate optical elements (MOE) are used as optical beam splitters with a specified spectral transmittance. MOE devices measure the magnitude of a property of a sample without measuring a spectrum. The difference between the transmittance and reflectance of an MOE is proportional to the chemical or physical property for which the regression pattern was developed. MOE devices mimic the performance of a full spectroscopy system using traditional analysis and multivariate data regression. Disclosed is an example of the use of MOE for estimating the concentration of two mutually interacting dye sample mixtures.

A further article on the topic of MOE devices is entitled *On-line Reoptimization of Filter Designs for Multivariate Optical Elements*, Halibach et al., Applied Optics, Vol. 42, No. 10, Apr. 1, 2003. pp. 1833-1838 and discusses fabrication of MOE filters.

Am article by Myrick et al. entitled *Application of Multivariate Optical Computing to Near-Infrared Imaging*, Proceedings of the SPIE, Vol 4577, 2002, pp. 148-157 discloses embedding a spectral pattern that corresponds to a target analyte in an interference filter in a beamsplitter arrangement. The chemical information in an image is obtained rapidly and with a minimal amount of computation. A candidate filter design that is tolerant to the angles present in an imaging arrangement is evaluated in near-infrared spectral region for an organic analyte and an interferent. All of the above articles are incorporated by reference herein in their entirety.

Still numerous other articles are available which disclose multivariate optical computing.

The present inventors recognize a need to evaluate petroleum as it is being drilled and flowing in a pipe to optimize decision-making during drilling and monitor flow assurance and other production characteristics of the fluid based on various parameters discussed above on the fly in real time as quickly and as automatically as possible so that corrective or preventive action may be immediately taken. The prior spectroscopic analysis techniques are not rugged and are relatively costly, slow, and generally require sampling offsite, i.e., external from and remote to the well or pipeline containing the petroleum.

Another problem recognized by the present inventors is the need to analyze petroleum that is flowing in real time and automatically as compared to prior art static samples used in traditional spectrometers.

A method for determining at least one property of crude petroleum comprises causing the petroleum to produce interacted light from incident light, performing a regression calculation on the interacted light with an optical calculation device responsive to the interacted light incident thereon to produce at least one output light signal manifesting the calculation and the corresponding at least one property; and determining the at least one property from the at least one output light signal.

In a further aspect, the step of performing the regression calculation includes generating first and second signals representing respective transmitted and reflected light from the optical calculation device and wherein said determining step includes processing the first and second signals.

In a further aspect, the step of performing the regression analysis comprises applying the interacted light from the petroleum to a plurality of stacked optical layers.

In a further aspect, the at least one property includes at least one of asphaltene, saturates, resins, aromatics, solid particulate content, hydrocarbon composition and content, gas composition C1-C6 and content, $CO_2$, $H_2S$ and correlated PVT properties including GOR, bubble point, density, a petroleum formation factor, viscosity, a gas component of a gas phase of the petroleum, total stream percentage of water, gas, oil, solid particles, solid types, oil finger printing, reservoir continuity, oil type, and water elements including ion composition and content, anions, cations, salinity, organics, pH, mixing ratios, tracer components, contamination, or other hydrocarbon, gas, solids or water property that can be related to spectral characteristics using regression methods.

In a further aspect, the causing and performing steps are performed in situ on a moving petroleum stream.

In a further aspect, the moving stream is in one of a drilling well and pipeline.

In a further aspect, the stream is flowing in a pipe or is flowing within a well to the surface in the drilling fluid or flowing from the subsurface formation into the well or into a tool or pipe within the well.

In a still further aspect, the causing and performing steps are performed on the crude petroleum flowing in a conduit wherein the flowing petroleum has a conduit fluid interface surface, further including repetitively and continuously reflecting light originating from a source onto the interface surface to produce the interacted light.

In a further aspect, the method includes generating spectroscopic data from the interacted light with a conventional spectroscopic instrument and then using that generated spectroscopic data for producing said optical calculation device.

Preferably, the method includes providing turbulence to the petroleum upstream the interface surface to provide homogeneous distribution of different petroleum components receiving reflected light.

In a further aspect, the method includes mechanically cleaning deposits from the crude petroleum on the conduit at the fluid interface surface.

Preferably the performing step includes applying the interacted light to a stacked layer of optical elements forming a multivariate optical calculation device.

In a further aspect, the method includes providing a plurality of multivariate optical calculation devices and applying the interacted light to each said device, each device corresponding to a different property to be determined.

Preferably, the causing step includes applying the incident light to an internal reflectance element wherein the light will repetitively interact with the petroleum with the internal reflectance element to provide multiple interactions for producing a total penetration of light into the petroleum an amount sufficient to manifest the at least one property.

In a still further aspect, the method includes providing an internal calibration to correct for drift in value of the calculation value and then determining the at least one property according to that corrected drift value.

A system for determining at least one property of crude petroleum according to a still further aspect of the present invention comprises an apparatus for applying incident light to the petroleum to cause the petroleum to produce interacted light. An optical calculation device performs a regression calculation on the interacted light, the device being responsive to the interacted light incident thereon to produce at least one output light signal manifesting the calculation and the corresponding at least one property. A signal processing arrangement determines the at least one property from the at least one output light signal.

In a further aspect, the calculation device includes a multivariate optical element that comprises a plurality of optical refraction layers, the layers manifesting a multivariate calculation wherein the result of the calculation correlates with a property of the petroleum.

In a further aspect, the petroleum is flowing in a pipe and has an interface surface with the pipe, the apparatus comprising a light source for providing the incident light to the petroleum interface surface at one location of the pipe and an internal reflectance element coupled to the pipe at the one location for applying the incident light to the interface surface and then alternatively receiving light from and reflecting light to the interface surface continuously from the applied incident light to generate the interacted light.

In a further aspect, a cleaning arrangement is included for cleaning the surface of the internal reflectance element at the interface surface.

In a further aspect, the system includes an indicator in the petroleum for indicating a parameter of the petroleum.

In a further aspect, a housing is included containing the apparatus and calculation device, the housing including a bellows for compensating for pressure differentials in the housing and in the petroleum.

In a further aspect, the petroleum is flowing in a pipe and the apparatus and calculation device are for producing the at least one output light signal in situ at the pipe.

Preferably a turbulence generator is in the pipe upstream from the apparatus.

In a further aspect, an in situ apparatus for assisting in maintaining flow assurance in a crude petroleum drilling field or pipeline based on at least one property of the petroleum flowing in the field or pipeline comprises an optical regression calculating apparatus associated in situ with one or more streams of the field or pipeline for generating at least one first output signal representative of the at least one property of the flowing petroleum flowing; and a processing arrangement remote from the calculating apparatus for processing the at least one signal and for generating an output signal manifesting the determined the property.

IN THE DRAWING

Figure 13:
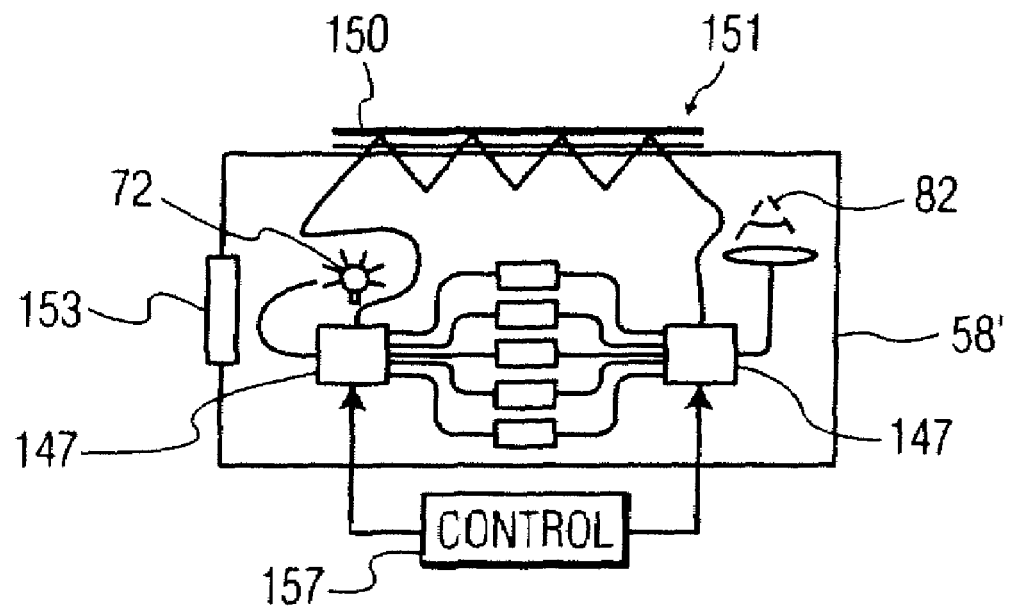
Figure 14:
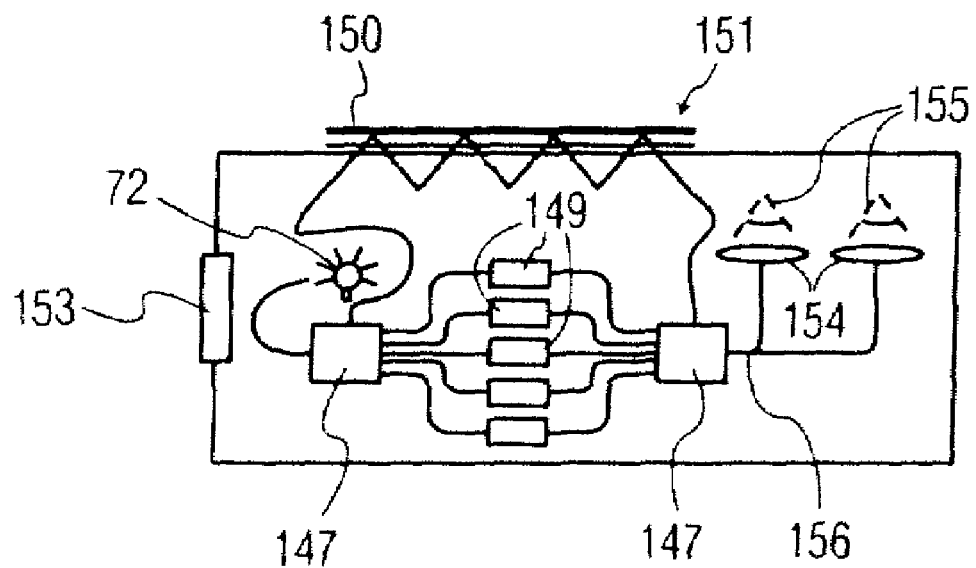

FIG. 13 is a diagram illustrating a further embodiment for pressure balancing the IRE-MOE analysis apparatus internal housing pressure with external pressures using an optically transparent fluid or closed path optics with an optically active fluid in the apparatus housing cavity; and FIG. 14 is a diagram illustrating the use of multiple MOEs for determining the presence of residuals in the crude petroleum which might affect the output determination.

Figure 1:
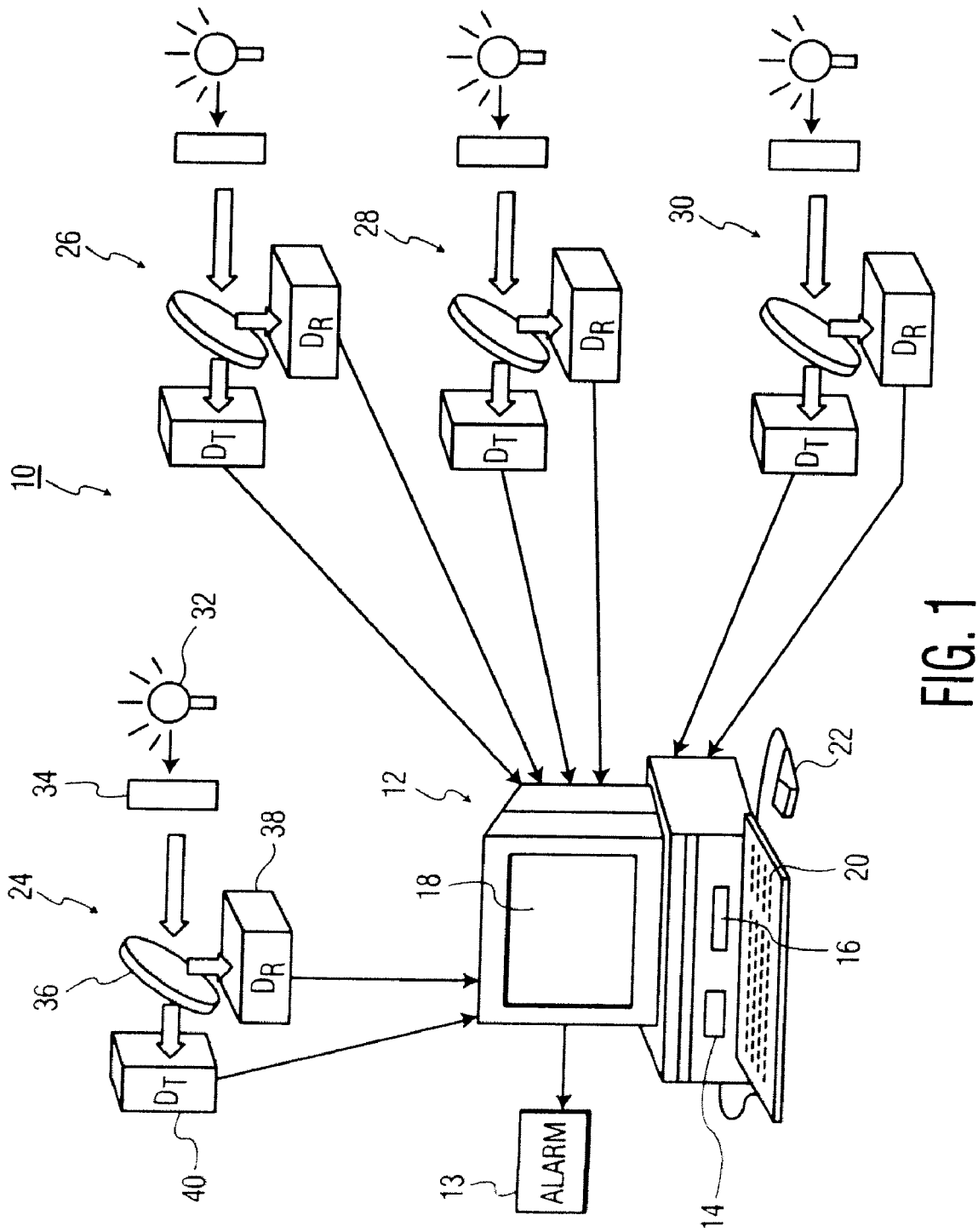
FIG. 1 is a schematic diagram of a system for monitoring crude petroleum in a petroleum field and/or pipeline(s) employing in situ optical regression calculation devices according to an embodiment of the present invention.

In FIG. 1, system 10 is used to determine a plurality of properties of crude petroleum either down hole in a drilling well or in a pipeline. When any of the determined properties is determined to possibly affect flow assurance of flowing petroleum in a drilling field or pipeline, issues an alarm as to that condition in real time and identifies the location of the condition. The term "property" means chemical or physical characteristic or element contained in the petroleum or which forms the petroleum composition and which includes, but is not limited to SARA (saturates, asphaltene, resins, aromatics), solid particulate content such as dirt, mud, scale and similar contaminants, $H_2O$ ion-composition and content, hydrocarbon composition and content, gas composition C1-C6 and content, $CO_2$, $H_2S$ and correlated PVT properties including GOR (gas-oil ratio), bubble point, density, a petroleum formation factor and viscosity among other properties listed in the introductory portion.

The term "down hole" means located in a well or a stream connected to a well or connected to any of one or more reservoirs whose fluids are subject to being pumped to the surface at a well. In practice, numerous reservoirs may be interconnected by a web of streams all feeding a common well head.

The term pipeline means a pipe employed to convey petroleum from a field well head to a remote location. Pipes are employed down hole and in pipelines. The term "pipe" includes down hole pipes or pipeline pipes. Down hole pipes may be vertical or horizontal or at other spatial relationships.

Residual is literally that which is left over. In regression analysis, the residual is that part of the data which can not be fitted by a regression.

Figure 5:
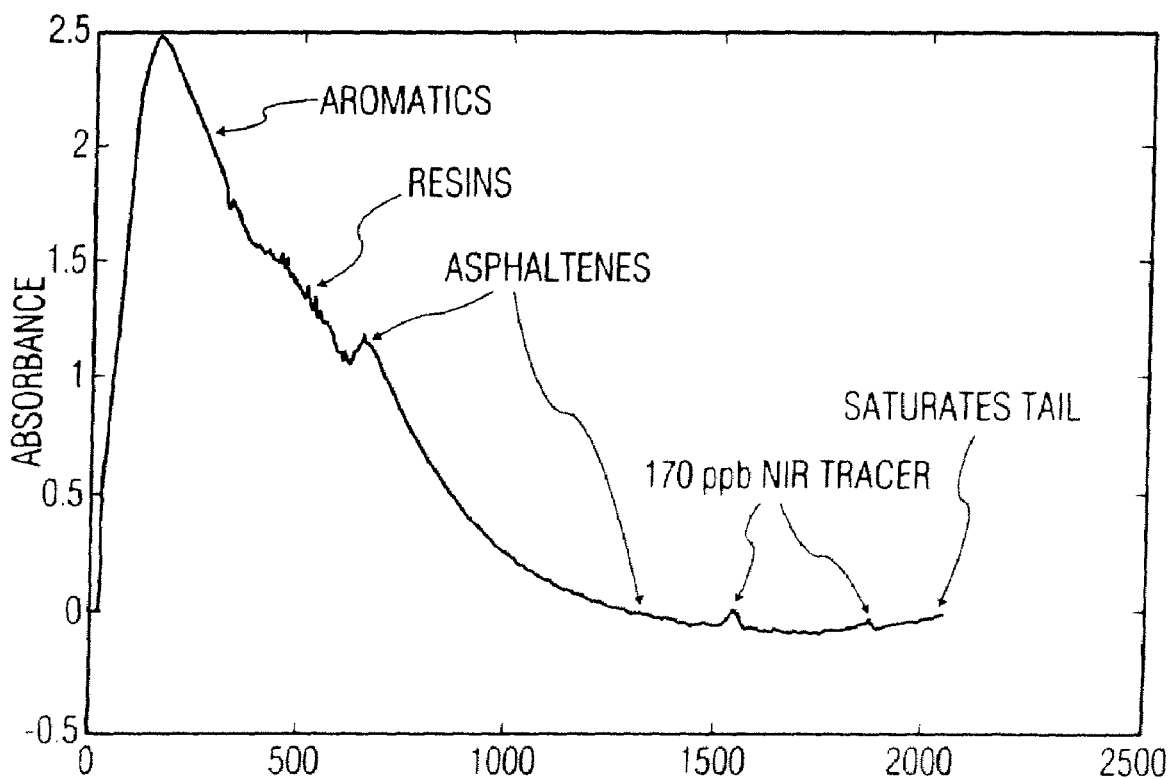
FIG. 5 is a graph of absorbance vs. wavelength representative of crude petroleum broad band spectra illustrating the principle component properties of the crude petroleum.

In FIG. 5, the broadband spectra of crude petroleum is shown to include aromatics, resins, asphaltenes, and saturates in which absorption is a function of wavelength. A 1270 ppb near infrared tracer (NIR) is shown at about 1500-1800 nm. The saturates are located at the high end of the spectrum.

System 10, unlike prior art systems, includes apparatuses located at and in contact with flowing crude petroleum and which components are located down hole or on a pipeline to determine in real time the properties of the petroleum which is flowing in pipes underground or in the pipeline. As a result, the apparatuses of the system 10 are subject to the extreme temperatures and pressures of the underground streams, but yet does not employ costly spectroscopic instruments as used in the prior art system, but rather rugged reliable optical calculation devices.

In FIG. 1, system 10 includes a programmed conventional computer 12 including a microprocessor 14, memory 16 which may include ROM and RAM for storing the analysis program and operating system program and determined data among other information as known in the art of spectral analysis as understood by one of ordinary skill. The computer 12 includes a display 18, a conventional input keypad 20 and a conventional mouse 22. The computer is located at central location remote from the remainder of the system 10 comprising optical petroleum property sensing and optical calculating analyzing devices 24, 26, 28, and 30. While four devices are shown, this number of devices is by way of illustration and more or fewer devices may be used in practice. Each device is for detecting and analyzing light interacted with the petroleum and corresponding to a different property of the petroleum of interest. Thus the system 10 may comprise as many calculating devices as there are properties in the petroleum to be determined, each device corresponding to a different property being monitored. The devices generally are preferably all located at or adjacent to a common stream location in the field or pipeline to provide an overall picture of the condition of the petroleum at that location and for identifying to the computer 12 the location of the device associated with a given property determination.

If the property determination is predetermined to be of a type and magnitude associated with a flow assurance problem, the computer 12 is programmed preferably to generate an alarm signal and activating alarm 13. The alarm 13 may be audio, a light, blinking or steady state or a display or any combination of these. In addition, the alarm may be a siren for example located in the field at any number of different sites for immediately alerting personnel to an immediate problem flow assurance condition that is presently being detected. The computer determines the unacceptable pipe flow condition detected by the associated analysis device(s). The alarm alerts personnel of the existence of a flow assurance problem that is being currently detected. The computer is programmed to provide information relating to the location and the nature of the problem based on the location of the optical calculating devices and associated apparatuses in the system 10.

The optical calculating devices 24, 26, 28 and 30 are rugged, can withstand the temperatures and pressures in situ at the pipes and thus are emplaced for long term permanent use. These devices are a marked improvement over present analyzing systems which are not rugged, are not automatic and are not for long term use, but rather are for short term use.

The number of four devices is arbitrary and is not intended to convey any significance. The number of devices in a system depends also on the number of pipes as well as the number of properties being monitored. It is contemplated that the number of devices of a system is not limited to measuring the properties of the petroleum at one location in one pipe. The computer 12 may be programmed to monitor a large number of devices associated with and located in respect of a number of different streams or pipes. Thus the properties of petroleum flowing independently in different pipes may be monitored simultaneously by one computer 12 which may also be programmed to correlate a number of different properties as being related to a flow assurance problem in one reservoir system. Of course more than one computer 12 may also be utilized for multiple systems in a complex field or pipeline.

The computer 12 is preferably coupled to an alarm output device 13 which may provide an audible alarm, a visual alarm or both.

For example, a map layout of the petroleum field or pipeline distribution network has the various branch streams identified by code or some form of labeling. The optical analysis devices are each associated with a code identifying the particular stream or pipe it is monitoring. The computer 12 analyses the optical analysis inputs for non-acceptable property situations and outputs the nature of the property and its location in the field or pipeline. With this information, immediate corrective action may be taken.

Preferably, one computer 12 may be used to monitor pipes in interconnected streams and reservoirs to provide an overall picture of the petroleum flowing to a common well head, for example. In this way, problems associated with one stream may be readily associated with corresponding streams feeding that one stream. The devices monitor similar properties of the different streams to determine the source of the problem property, i.e., the stream(s) or reservoirs(s) exhibiting the same potential problem instantaneously. Thus the computer may be programmed to display and indicate a possible source of a problem by analyzing similar properties from common interconnected streams and reservoirs. This readily simplifies the problem of which streams to monitor and log as compared to the prior art costly and complex spectroscopic systems.

Each of the devices 24, 26, 28 and 30 comprises similar elements so that a description of one device 24 is representative. Each device is arranged to determine one property of the crude petroleum. The properties determined include any of those depicted above, but preferably include at least the more important constituents where importance is field dependent. Other properties of course are also sensed and detected by still other devices (not shown in FIG. 1).

It should be understood that a given pipe will be associated with as many devices such as devices 24 and so on as deemed appropriate for a given stream, location and reservoir. It is known, for example, that different reservoirs may exhibit fluids and solids with different detrimental properties such as chemical potential for scale, watering, hydrates etc. Once these properties are determined for a given reservoir, then it may not be necessary to monitor for all properties depending upon the findings relative to that reservoir, stream, pipeline and so on. Such properties may be monitored on a scheduled basis, for example, using a pig, a device including but not limited to a robot designed to go down hole or in a pipeline and perform work, carrying one or more devices such as device 24 or may be fixed in place to each pipe stream.

The importance of the present system 10 is that the devices 24, 26, 28, and 30 are relatively low cost and rugged and thus can be implemented in many more locations and streams than otherwise possible with prior art systems.

Representative device 24 comprises a light source 32, the petroleum 34 being monitored which should be understood to be flowing as a stream in a pipe and is not a static sample as depicted in FIG. 1, a multivariate optical element (MOE) 36 which is an optical regression calculation device, a detector 38 for detecting light reflected from MOE 36 and a detector 40 for detecting the light transmitted by MOE 36. The MOE is a unique optical calculation device that comprises multiple layers.

Figure 4:
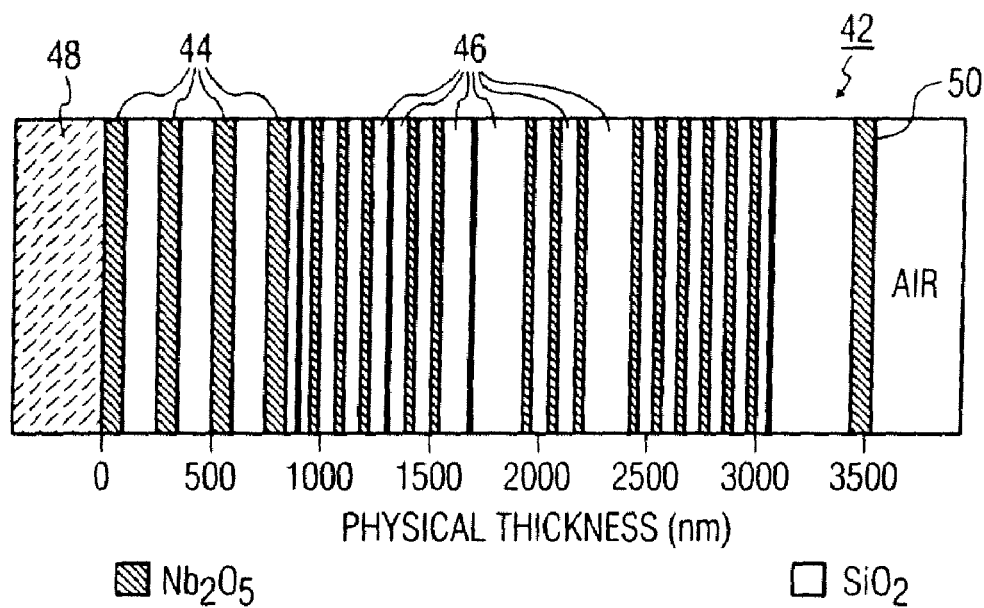
FIG. 4 is a side elevation sectional view of an illustrative representative MOE filter construction.

In FIG. 4, for example, representative optical regression calculating device MOE 42 comprises a plurality of alternating layers 44 and 46 respectively of $Nb_2O_5$ and $SiO_2$ (quartz). The layers are deposited on a glass substrate 48 which may be of the type referred to in this art as BK-7. The other end layer 50 of the optical calculating layers is exposed to the environment of the installation. The number of layers and the thickness of the layers are determined from and constructed from the spectral attributes determined from a spectroscopic analysis of a property of the stream using a conventional spectroscopic instrument. The combination of layers corresponds to the signature of the property of interest according to the spectral pattern of that property.

The spectrum of interest of a given property typically comprises any number of different wavelengths. It should be understood that the MOE of FIG. 4 does not in fact represent any property of crude petroleum, but is provided for purposes of illustration only. The number of layers and their relative thicknesses of FIG. 4 thus bear no correlation to any crude petroleum property to which the present invention is directed and are also not to scale. The thickness of the layers may be in the order of microns each as shown.

As discussed in the aforementioned '276 and '531 patents, the multiple layers have different refractive indices. By properly selecting the materials of the layers and their spacing, the optical calculation device can be made to selectively pass predetermined fractions of light at different wavelengths. Each wavelength is given a predetemined weighting or loading factor. The thicknesses and spacing of the layers may be determined using a variety of approximation methods from the spectrograph of the property of interest. As disclosed in the aforementioned patents, these methods may include inverse Fourier transform (IFT) of the optical transmission spectrum and structuring the optical calculation device as the physical representation of the IFT. The approximations convert the IFT into a structure based on known materials with constant refractive indices. These Patents state that information regarding the structures of such optical calculation devices is provided at Applied Optics, Vol. 35, pp. 5484-5492 (1996) and Vol. 129, pp. 2876-2893, incorporated by reference herein and also may be provided as noted in the introductory portion herein by the National Research Council of Canada.

The weightings that the MOE 42 layers apply at each wavelength are set to the regression weightings described with respect to a known equation, or data, or spectral signature which is given in these patents. The optical calculation device MOE 42 performs the dot product of the input light beam into the optical calculation device and a desired loaded regression vector represented by each layer for each wavelength. The MOE 42 output light intensity is directly related to and is proportional to the desired petroleum property. The output intensity represents the summation of all of the dot products of the passed wavelengths and corresponding vectors.

If the property is resin in crude petroleum, for example, and the regression vectors are that of the resin, the intensity of the light output of the MOE is proportional to the amount of resin in the sample through which the light beam input to the optical calculation device has either passed or has been reflected from or otherwise interacted with. The ensemble of layers corresponds to the signature of resin. These wavelengths are weighted proportionately by the construct of the corresponding optical calculation device layers. The resulting layers together produce an optical calculation device MOE 42 output light intensity from the input beam. The output light intensity represents a summation of all of the wavelengths dot products and the loaded vectors of that property, e.g., resin. The output optical calculation device intensity value is proportional to the amount of resin in the crude petroleum being examined. In this way an MOE optical calculation device is produced for each property to be determined in the crude petroleum.

A further description of the MOE optical calculation devices and their construction can be found at the internet web site:http://nanonet.research.sc,edu/videos/myrick_MOC_files/default.htm., which is a lecture given by Dr. Michael Myrick on this subject, an inventor in the above referred to patents and in his articles referred to in the introductory portion including those entitled *Multivariate Optical Elements Simplify Spectroscopy and Application of Multivariate Optical Computing to Near-Infrared Imaging*, both incorporated by reference herein.

Such MOE optical calculation devices represent pattern recognition devices which produce characteristic output patterns representing a signature of the spectral elements that define the property of interest. The intensity of the light output is a measure of the proportional amount of the property in the test media being evaluated. For example, an MOE transmission output waveform might appear as in FIGS. 7 and 8, which do not represent any petroleum property, but are shown for purposes of illustration only. The waveform of FIG. 7 forms a pattern comprising different wavelengths of a spectrum that is unique to a property. This waveform may be the light that impinges upon detector 40, FIG. 1, for example, or the corresponding detectors of devices 26, 28 and 30 of the system 10. Each of these detectors, such as detectors 38 and 40 associated with MOE 36, transmits its output, an electrical signal, which represents the magnitude of the intensity of the signal of FIG. 7 that is incident on the detector. This signal thus is a summation of all of the intensities of the different wavelengths incident on the detector. The various weighting factors assigned to each layer produce a composite signature waveform for that property.

Figure 7:
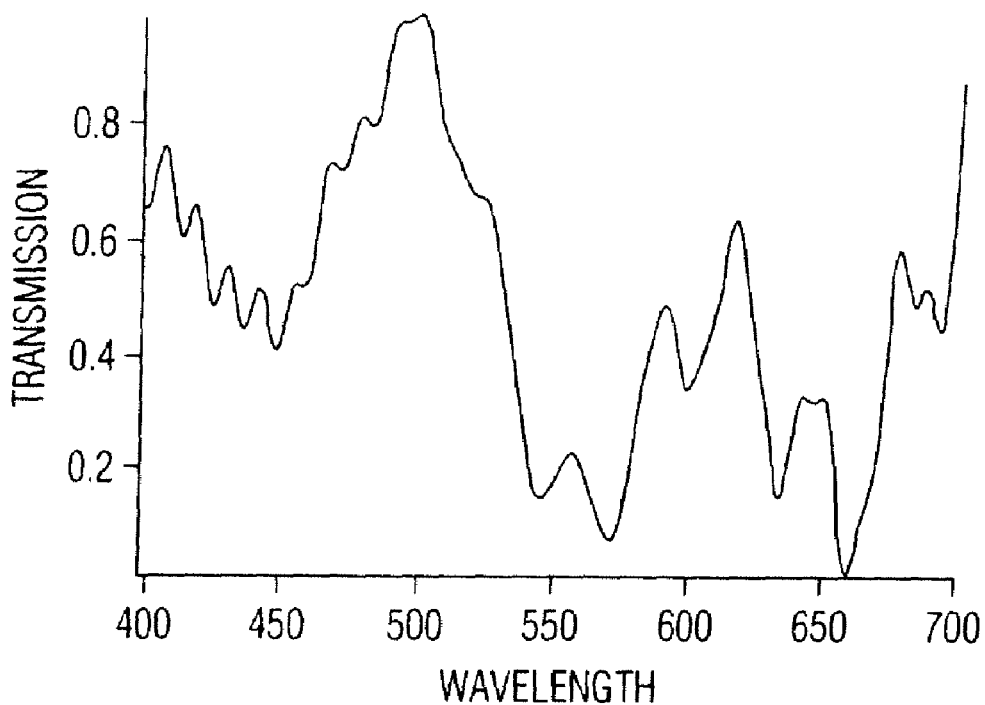
FIGS. 7 and 8 are illustrative curves illustrating respective transmission and reflectance light intensity signature patterns of a an illustrative substance property passed by a multilayered MOE filter.
Figure 8:
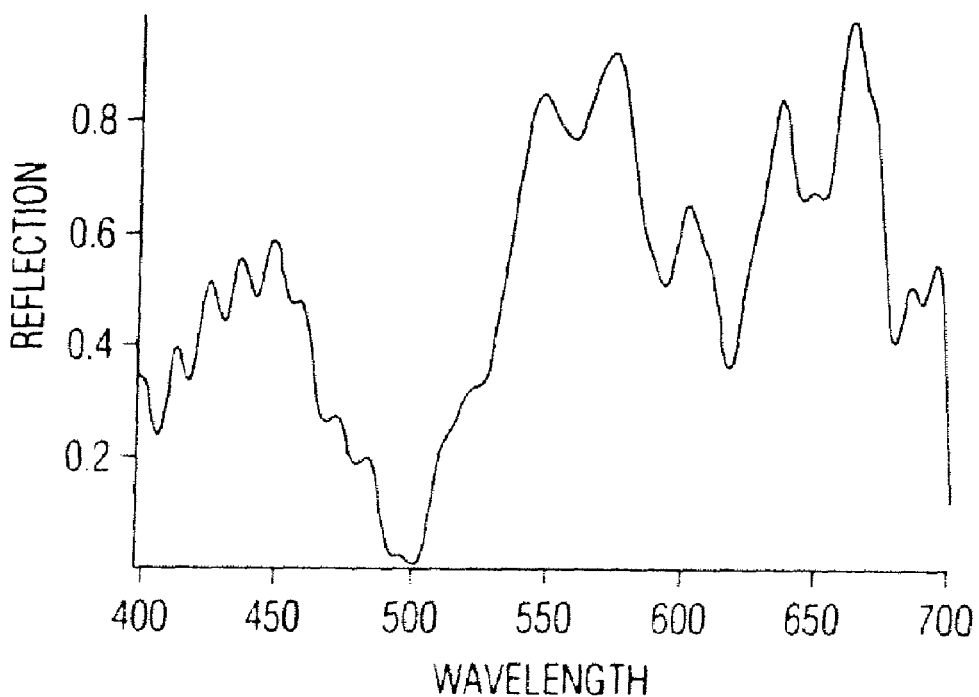

The reflected light from the MOE 36, FIG. 1, produces a negative of the transmitted signal of FIG. 7 for no sample or optical absorbance. This reflected signal is represented by the waveform of FIG. 8 and is not a regression calculation. The reflected signal is subtracted from the transmitted signal of FIG. 7 by the computer 12, FIG. 1. The difference represents the magnitude of the net light intensity output from the MOE and the property in the petroleum being examined. This subtraction provides correlation that is independent of fluctuations of the intensity of the original light due to power fluctuations, or use of different light bulbs, but of the same type as used in the original apparatus. That is, if the transmitted light intensity varies due to fluctuations, the system could interpret this as a change in property. By subtracting the negative reflections, the result is an absolute value independent of such fluctuations and thus provides needed correlation to the desired property being determined. Either the raw detector outputs may be sent to a computer, or the signals may be subtracted with an analog circuit and magnified with an operational amplifier converted to voltage and sent to the computer as a proportional signal, for example.

Figure 6:
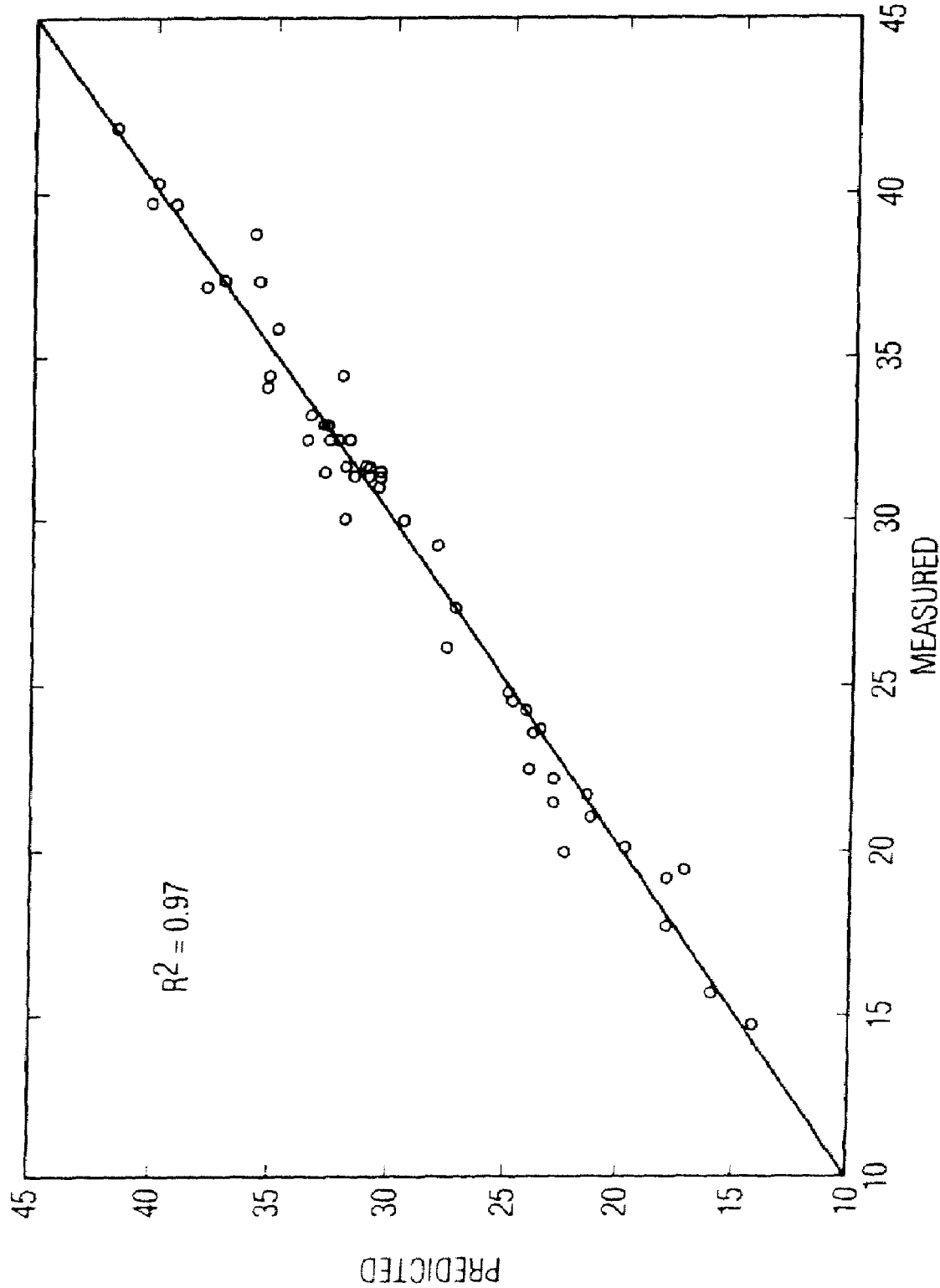
FIG. 6 is a regression curve for the aromatics crude petroleum component property showing correlation of the measured and predicted values using partial least squares (PLS) wherein $R^2=0.97$ shows the percentage variance captured.

There is good correlation between the predicted property such as aromatics, for example, in FIG. 6, and the measured amount of property. Thus a method has been described for determining at least one property of crude petroleum comprising causing the petroleum to produce interacted light from incident light; performing a regression calculation on the interacted light with an optical calculation device responsive to the interacted light incident thereon to produce at least one output light signal manifesting the calculation and the corresponding at least one property; and determining the at least one property from the at least one output light signal.

Figure 2:
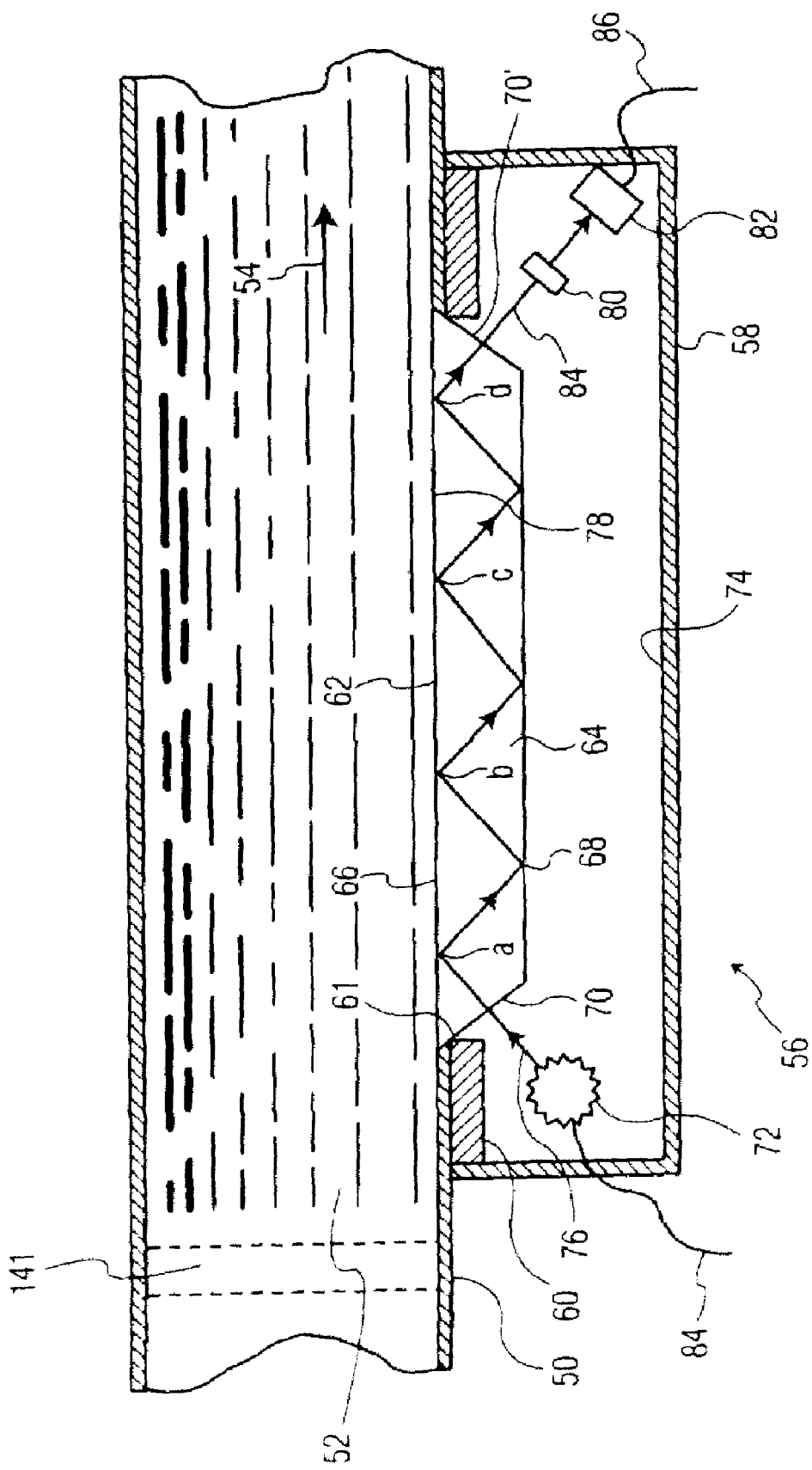
FIG. 2 is a sectional elevation view of a pipe in which crude petroleum is flowing and a representative property monitoring system according to a further embodiment of the present invention and including a portion of the embodiment of FIG. 1.

In FIG. 2, a representative pipe 50 may be part of a pipeline or a down hole pipe in a petroleum field. The down hole pipe may be a vertical pipe or horizontal pipe and may be part of the well head or interconnecting stream pipes that interconnect various reservoirs of petroleum in a field. Petroleum 52 and/or associated water gas is flowing in the pipe in direction 54. Attached to the pipe 50, which may be stainless steel, is an optical in situ MOE crude petroleum property detecting apparatus 56. Apparatus 56 corresponds to one of the devices 24, 26, 28 and 30 of FIG. 1, and is utilized in a system such as system 10 shown in FIG. 1 for determining the amount of a property of the petroleum flowing in the pipe 50. The system corresponding to system 10 utilizing the apparatus 56 determines the amount of the property in real time and reports that amount instantaneously as it occurs in the flowing stream of petroleum 52 and simultaneously with other apparatuses (not shown) corresponding to apparatus 56 attached to pipe 50 adjacent to or at a given location in the pipe and still other pipes corresponding to numerous steams in the field being monitored.

The apparatus 56 comprises a housing 58, which may be magnetized metal or stainless steel, and a frame 60, which may be stainless steel, and which also may be magnetized and which may have appropriate protective coatings. The housing 58 and frame 60 maybe circular cylindrical or rectangular. The housing is preferably magnetic so that it is readily attached and detached from the metal pipe 50 in one implementation, but may be attached in other ways in other implementations. The pipe 50 has a circular or rectangular opening 62 forming a window that is transparent to light including the IR spectrum. The housing 58 and frame 60 are circular cylindrical, the frame forming an internal circular opening 61.

An internal reflectance element (IRE) 64, which can be a circular cylindrical optically transparent disc or rectangular optically transparent prism, or other shapes as may be used in a particular implementation, preferably of clear optically transparent diamond, or a pair of spaced optically transparent plates (not shown), is attached to the frame 60 in the frame opening 61 enclosing and sealing the opening 61. The IRE may be bonded to the frame, for example, or attached in other ways as known in this art. The IRE 64 has two spaced parallel planar surfaces 66 and 68 and an outer annular inclined facet 70 defined by the Brewster angle, dependent upon the materials of the interface and wavelength of the light, to the surfaces 66 and 68. A light source 72 is located in the housing cavity 74 and is located to cause its light 76 to be incident on the facet 70 at a right angle thereto. The facet is also at the Brewster angle or about 45° to the surface 78 of the petroleum 52 flowing in the pipe 50 contiguous with the IRE surface 66. The IRE 64 and frame 60 seal the pipe opening 61 in conjunction with a gasket such as an O-ring (not shown). The magnetic force between the housing 58 and frame 60 to the pipe 50 is sufficiently high to withstand the anticipated pressures of the flowing petroleum 52.

Located in the cavity 74 of the housing 58 is a MOE optical calculation device 80 and a detector 82 responsive to the output of the optical calculation device 80 for generating an electrical intensity output signal whose value corresponds to a property of the petroleum to be determined. A conductor 84 supplies power to the light source 72 and a conductor 86 receives the detector output signal. Pipes in some petroleum fields are presently wired in many instances for such power and signals. Wires such as conductor 86 may be connected to a computer such as computer 12, FIG. 1, located at a remote station for determining the property of the petroleum manifested by the signal on conductor 86. A transparent fluid (not shown) in the housing cavity 74 may be pressurized to balance the pressure of the petroleum in the pipe 50 to prevent leakages therebetween. In the alternative to hard wiring the apparatus 56 components, a battery, a local generator or telemetry could also be used to power the apparatus components.

Figure 10:
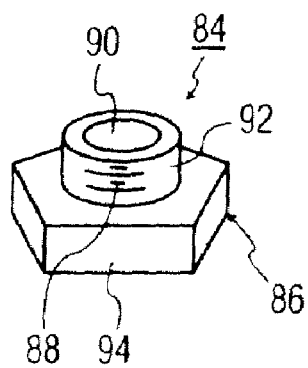
FIG. 10 is an isometric view of an alternate embodiment of the housing for the optical arrangement of FIG. 2.

In the alternative, an apparatus 84, FIG. 10, corresponding to apparatus 56 of FIG. 2, may be in the form of a bolt 86. The bolt 86 forms a housing such as housing 58 of FIG. 2. The bolt 86 has external threads 88 and is threaded to mating pipe threads (not shown) such as would be formed in pipe 50 in the pipe opening such as opening 61. The threads may be sealed to the pipe threads with a thread sealant. An IRE 90 is attached to the end of the bolt shank 92 which is hollow. The other components of the apparatus 56 of FIG. 2 are located in the hollow interior of the shank 92. The bolt has a hex head 94 for attaching the bolt to the mating pipe.

One problem with spectroscopy of raw petroleum or "oil" is the large absorbance of crude petroleum. Crude petroleum looks black because most of the light at all visible wavelengths is absorbed through even by very small amounts of the petroleum. Some crude petroleums such as condensates and some "light" oils are more transparent in the visible wavelength range, but the majority of oils are dark. Experiments have shown that path lengths through which visible light must travel to obtain an optimum signal vary from 20 to 60 micrometers. Experiments have shown that for dark oils, a 40 micrometer path length is acceptable. For the infrared region of absorption, optimum path lengths are a little longer as crude petroleum is more transparent in this region. However up to the electromagnetic region of 2.5 micrometers in the infrared, path lengths are still limited to between 100 and 300 micrometers (0.1 to 0.3 millimeters). Crude oil or petroleum prior to treatment is a dirty material containing both solid particles of varying diameters and multiphase "bubbles" (water in oil, oil in water, gas in oil, gas in water). Both the solid particles and the "bubbles have the capacity to clog a conventional absorption spectroscopy setup in which light is passed through a set of sampling windows to a detector.

One property of light as a wave is the ability of light to change its direction at a boundary through reflection. In reflection, the angle of reflection is equal to the angle of incidence as measured from the perpendicular of the boundary surface. At a given angle whether the wave will be transmitted or reflected in the optical domain is determined by the index of refraction of the materials at the boundary as well as the angle of incidence. For a system, reflection follows the behavior that the shallower the angle of incidence, the greater the chance of reflection and the greater the difference between index of refractions, the greater the chance for reflection. For some materials index of refraction may be chosen such that total internal reflectance is achieved and all light at almost any angle will be reflected. The exception is when light hits the boundary at the Brewster angle.

Using this principle fiber optics carry light with little transmission loss through curved paths. Because the reflection occurs at the boundary which may have a very fine transition zone (angstrom level) which acts as sharp for light with a wavelength in the visible to infrared, the reflection actually takes place in the material behind the boundary from approximately 0.3 to 5 micrometers. This principle has led to the development of a spectroscopic sampling technique called total internal reflectance and makes use of a device called an internal reflectance element (IRE). In this device light is passed into a material of extremely high index of refraction usually diamond or sapphire. The light bounces between two boundaries one containing the sample, and the other containing an optically transparent material. As light passes behind the sample boundary some of the light interacts with the sample as determined by normal spectroscopy. The total number of multiple reflections controlled by the element length is used to build any desired path length.

For instance at a one micrometer sampling depth, forty (40) reflections could build up a path length of forty (40) micrometers. Because the IRE sampling method does not suffer the constriction of a more conventional absorbance spectroscopy method, the device will not clog readily. IREs are commercially available.

Companies that manufacture IRE can be found on the internet web at:

http://www.tydex.ru/products/products4/ATR.html
http://www.goaxiom.com/datasheets/tnl_ds.htm
http://www.wilksir.com/pdf/in-linesensorsheet.pdf For a discussion on theory of IREs see:
http://www.mellesgriot.com/products/optics/oc_2_1.htm
http://www.pacwill.ca/reflect.htm
http://www.wilksir.com/idf/in-lineinfraredtech.pdf All of the above are incorporated by reference herein in their entirety.

In operation of the apparatus 56, FIG. 2, the light 76 from the source 72 is transmitted by the IRE to the surface 78 of the flowing petroleum in the pipe 50. It is known that the light 76 incident on and reflected from the petroleum surface will penetrate the surface a few micrometers, e.g., 0.3-5 microns, as discussed above. It is also known as discussed above that penetration of light into the petroleum must be to at least a depth of, or equivalent thereof, about 40 microns in order for the reflected interacted light from the petroleum surface 78 to carry sufficient wavelength information about the petroleum properties to be meaningful. Less penetration results in insufficient data being carried by the reflected interacted light to appropriately determine a property of the petroleum in the pipe. The total path length requirements change depending upon the petroleum type, gas phase, water phase, the component being analyzed and so on.

As a result, the light 76 from the source 72 is reflected from the petroleum surface 78 and which penetrates the surface to about 5 micrometers at location a. This reflected light from location a is interacted light and is reflected to the inner surface of surface 68 of the IRE to produce further interacted light. Refraction indices of the diamond of the IRE 64 cause the interacted light to be reflected from the surface 68 back through the IRE to the petroleum surface 78 at location b again penetrating to a depth of about 5 micrometers. This reflection process is repeated at locations c and d and other locations (not shown) until an accumulated depth of about 40 micrometers for all of the interactions is achieved. At the last location d, in this example, the reflected interacted light from the petroleum surface 78 is incident on IRE facet 70 at location 70'. Here the reflected light 84 is normal to the facet of the IRE 68 and passes through the facet 70'.

The light 84 is incident on the MOE 80 and passes through the MOE 80 to detector 82. It should be understood that a second detector (not shown) is also responsive to reflected light from the MOE and supplied to a further conductor (not shown) and thus to the computer such as computer 12, FIG. 1, as described above.

A separate apparatus 56 is provided for each property to be determined from the flowing petroleum. The IRE element 64 may have a thickness of about 1-2 mm and a diameter of about 10-20 mm when fabricated of diamond. Since commercially available IRE elements are available in housings that are threaded to petroleum pipes in the form of a hex head bolt similar to that of bolt 86, FIG. 10, it is convenient to alter the fabrication of such devices to include a detector and MOE as well as the IRE reflectance element as depicted in FIG. 2 and as described above in connection with FIG. 10.

The housing of such a commercially available IRE device is in the form of a hex head bolt with the optical diamond element at the tip of the bolt remote from the head. The shaft and head are optically transparent to receive reflected interacted light from the surface of the petroleum for transmission to an external device. It is a simple physical alteration to include the additional components of FIG. 2 in such a commercially available device and add the necessary electrical conductors for the light and detector currents as described However, it should be understood that the distribution of light associated with the various light paths between the light source 72, FIG. 2, and the IRE 74 is critical to the construction of the MOE 80. That is, different housings, sources attached to such housings, and IRE associated therewith all have unique light paths that may affect the light distribution. These light paths and distributions need to be taken into consideration during the MOE construction. This construction is based on a representative spectrum for the petroleum of interest. The intensities and distribution of the various wavelengths may vary from apparatus to apparatus and thus such light paths and distributions need to be taken into consideration in the design and construction of the MOE associated with a given apparatus.

This problem is resolved by using the housing 58, light source 72 and IRE 74 that is eventually to be utilized for the optics associated with a given MOE for use in generating the spectrum that is to be provided by a traditional spectrometer. That generated spectral data is then utilized to construct the MOE that is to be utilized with the associated housing, light and IRE components. Thus it is assured that the light paths and distributions from the installed housing, light source and IRE are identical to those used to create the MOE and thus there will be no errors or problems in utilizing the MOE with such components. Thus if such components ever need replacement, a new MOE needs to be constructed unique to those replacement components or otherwise compensated for changes in light distributions. Otherwise an error in property determination may be possible if other components are utilized other than those used to create the MOE. Thus any components utilized in or that may affect the optical path lengths or wavelength distributions from light source to MOE need to be utilized to determine the spectral aspects of the property of interest used to construct the corresponding MOE.

Use of Abrasive Cleaning With IRE

A second major problem with optical sensor measurement of crude petroleum, is deposit buildup on the windows in the pipe. Part of this problem is minimized by the use of diamond for the IRE 64 material (FIG. 2). Diamond is chemically inert, scratch resistant, thermally stable, pressure stable, and can be made extremely smooth. Because it is chemically inert it is believed that chemical adhesion to the surface of the IRE is minimized. Because the surface can be made extremely smooth it is believed that physical adhesion is also minimized. Because diamond is scratch resistant, it is believed that the diamond will continue to be smooth over long periods of time allowing it to continue to resist physical adhesion. Still there is the possibility for some deposits to build up. It is believed that these deposits will be loosely bound and therefore easily removed.

In many of the desired applications for MOE technology including down hole use, access to the IRE will not be available requiring a remote or automated cleaning capability. Since diamond is scratch resistant, an abrasive cleaner is contemplated. Because of relative inaccessibility of the IRE, the IRE cleaning device should be reusable such as a wire brush, but more durable such as a stainless steel brush (many of these environments are corrosive and would dissolve simple brushes).

Another embodiment is to use a Teflon scraper, Metal (stainless steel) scraper, or ceramic scrapper for cleaning the window in combination with the sand and carbonate particles always present in a crude oil flow. Mechanical force is added to perform the abrasive cleaning action. Mechanical energy in a flow stream may be gathered directly from the flow stream to perform the cleaning action.

Figure 2A:
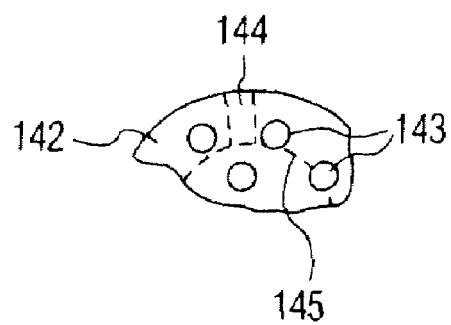
FIG. 2a is a fragmented front elevation view of a turbulent generator for use in the embodiment of FIG. 2.
Figure 2B:
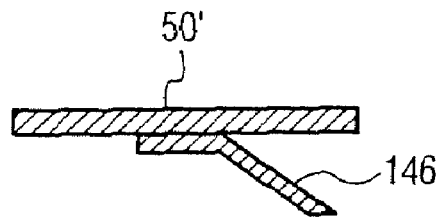
FIG. 2b is a side elevation view of a representative turbulent generator according to a further embodiment for use in the embodiment of FIG. 2.
Figure 2C:
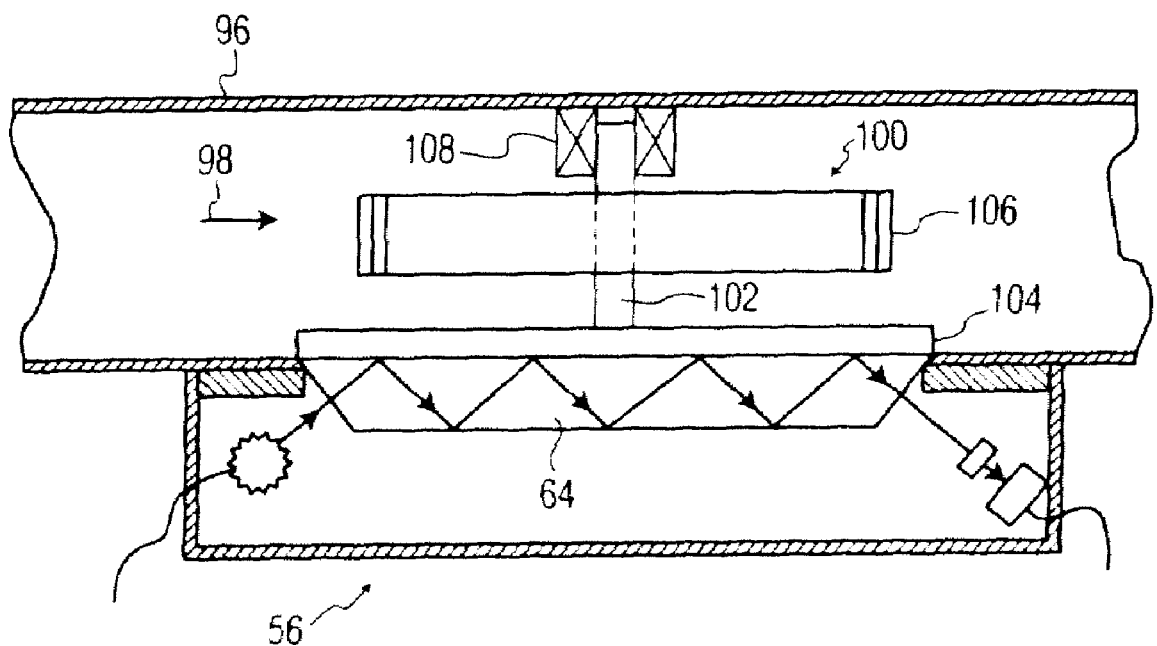
FIG. 2c is a sectional elevation view of a pipe in which crude petroleum is flowing similar to FIG. 2 according to a further embodiment of the present invention including a side elevation view of a turbine device for cleaning petroleum deposits from the surface of an internal reflectance element (IRE)
Figure 2D:
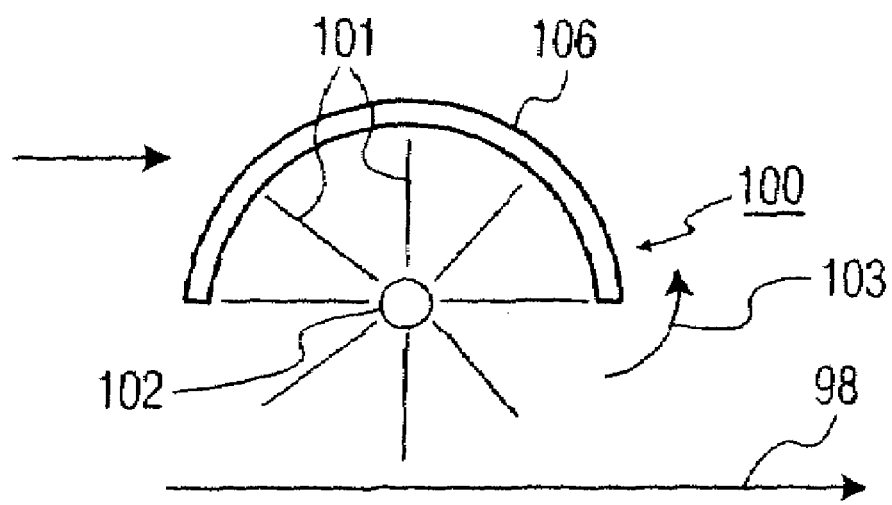
FIG. 2d is a plan view of the turbine device of FIG. 2c.
Figure 3:
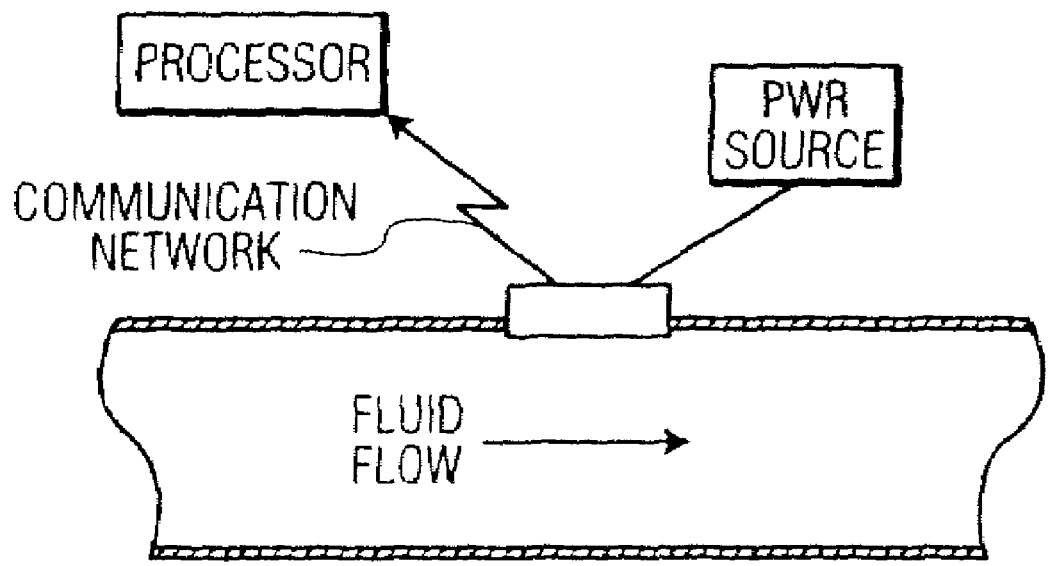
FIG. 3 is a sectional elevation side view of a portion of a petroleum pipe illustrating a diagrammatic representation of the embodiment of the present invention depicted in FIG. 2.

In FIG. 2c, a pipe 96 has petroleum flowing in direction 98. Optical analysis apparatus 56 is attached to the pipe as discussed in connection with FIG. 2. A turbine 100 is driven by the petroleum stream flow. The turbine 100 has blades 101 to rotate shaft 102 connected to a steel wire brush 104 (or Teflon scraper, not shown). The shaft 102 is rotatably connected to the pipe 96 by bearing 108. In FIGS. 2c and 2d, the turbine 100 is located within a semicircular flow deflector 106 which directs the fluid flow against the blades 101 for rotation in direction 103.The flow induces rotation in the turbine 100 which rotatably slides the brush 104 over the surface 66 of the IRE 64. The turbine and shaft designs may vary according to a given implementation. In keeping with the discussion above regarding utilization of the components of the optical apparatus to construct the corresponding MOE, if a turbine is used, then such a turbine preferably must be used to obtain the spectral properties of the petroleum of interest used to construct that MOE. Also, any other device utilized in the optical apparatus corresponding to apparatus 56 must also be used to determine the spectral properties of interest used to construct the corresponding MOE as such other devices may also adversely affect the light path lengths or distributions and thus the calculated output of the MOE.

Fiber optics (not shown) may also be used in the apparatus 56 as part of the light paths.

In the alternative, a reciprocating mechanism (not shown) may be provided for reciprocating the brush such as brush 104 or a scraper (not shown) over the IRE surface.

Figure 9:
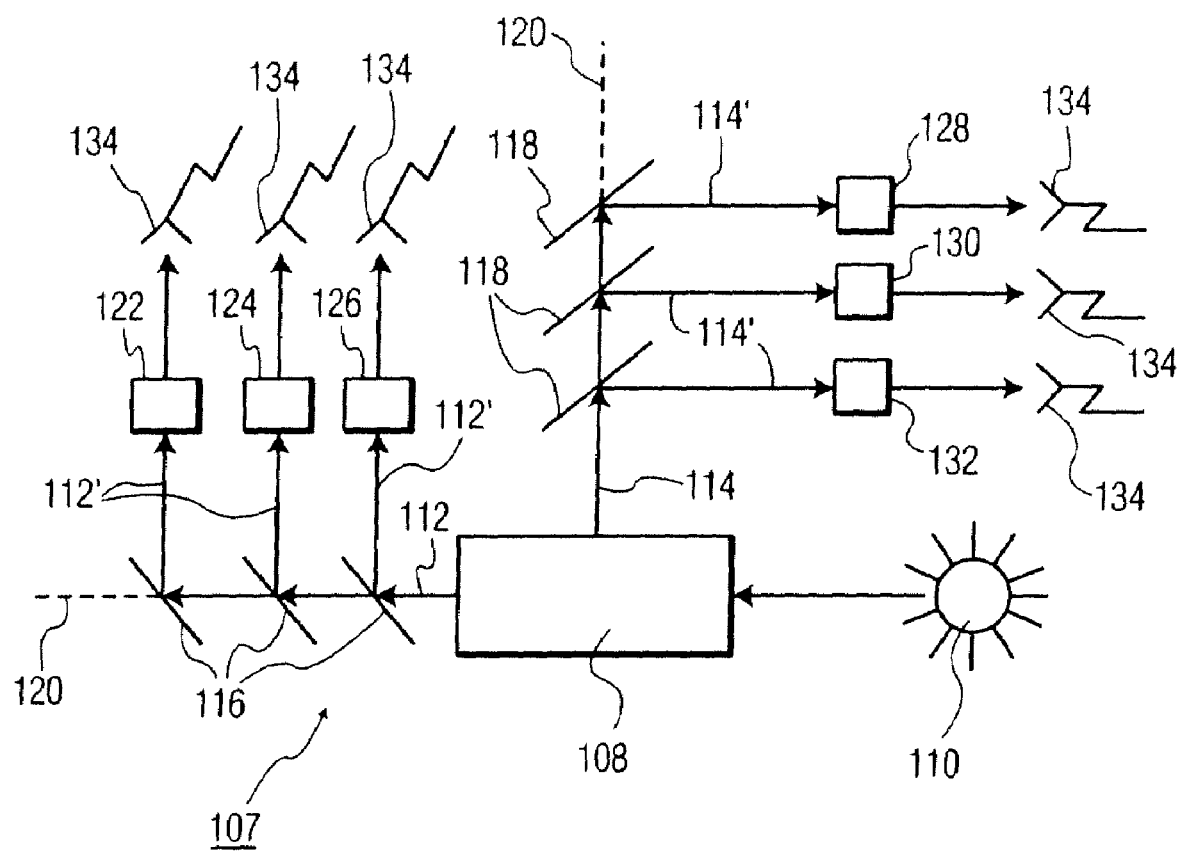
FIG. 9 is a diagrammatic representation of a system employing a plurality of MOE analysis devices for determining a property of a crude petroleum sample employing both absorbance and fluorescence spectra and a plurality of MOE analyzing arrangements.

In FIG. 9, an alternative embodiment is illustrated utilizing a system 107. System 107 comprises a petroleum sample 108. A light source 110 provides light to the petroleum sample 108, the light passing through the sample 108. Beam 112 represents absorbed light and beam 114 represents florescence or other emissions. Emissions may occur by applying energy not necessarily light to the petroleum. The IRE relates to light absorption. But, in the case of emissions, different apparatus may be used. Beam 112 is reflected from mirrors 116 and redirected 90°. The mirrors 116 are partially transmissive forming partially reflected beams 112'. Beam 114 is reflected from partially transmissive mirrors 118 forming partially reflected beams 114'. While three beams 112 and three beams 114 are shown, in practice more (or fewer) than three beams may be utilized as represented by the dashed lines 120. The reflected and transmitted beams are not frequency biased.

The reflected beams 112' are directed to a corresponding MOE 122, 124 and 126. The reflected beams 114' are directed to a corresponding MOE 128, 130 and 132. The output signals of the MOEs are detected by detectors 134 whose outputs are analyzed by a computer (not shown). By way of example, four different spectrums are analyzed by the absorbance MOEs 122-126 and so on and similarly by the florescence or emission sensitive MOEs 128-130 and so on. This system thus obtains four, for example, different measurements on four different properties, asphaltene, resins etc. at the same time. The outputs of the detectors 134 associated with beams 112 and 114 results in a property that is proportional to the sum of two MOE detected signals, one from each spectroscopic absorbent and fluorescent component which represent one property. Thus four different properties are analyzed with both an absorbent and/or a fluorescent (emissive) beam.

Multiple phase flow is often heterogeneous with segregation along phase densities and viscosities. For example solids sludge to the bottom of a pipe, gas floats to the top, and oil rides on top of water. Lower viscosity fluids tend toward the center of the pipe while higher viscosity tend toward the rim of the pipe. This segregation is often only slight, but none the less important to consider. Because petroleum flow is often multiple phase flow, it is believed necessary to achieve homogeneous sampling when absolute measurements, especially when between phases, analysis is desired. Separation in flow occurs most often for laminar flow. Therefore, if turbulent flow is introduced in the flowing petroleum upstream of the optical analyzers, then homogeneous sampling will be more probable.

Turbulent flow is best induced over short distances by an obstruction or constriction in the pipe. The actual dimensions of the obstruction depend on the viscosity of the fluids in flow, the diameter of the pipe, and the speed of the fluid. The actual dimensions of the obstruction may vary from one application to another, but can be easily designed using commercial design packages such as "Stateflow," a computer program commercially available from Mathworks Company. Other computer programs available are Flowmaster from Flowmaster International Limited, Sate SRL from Fluid Systems Simulation Services and Hydraulic Blockset from Expert Control GmbH.

A constriction in a pipe increases the flow rate or velocity within the constriction and thereby induces turbulent flow. This method of turbulent flow induction has the advantage of "rushing" the petroleum being sampled past the window of the IRE. The turbine driving the scraper or brush, FIG. 2c, that is cleaning the window is also rotated at a higher rate as a result of increased flow velocity due to the constriction. Both actions are believed to help keep the IRE window clean.

Figure 11:
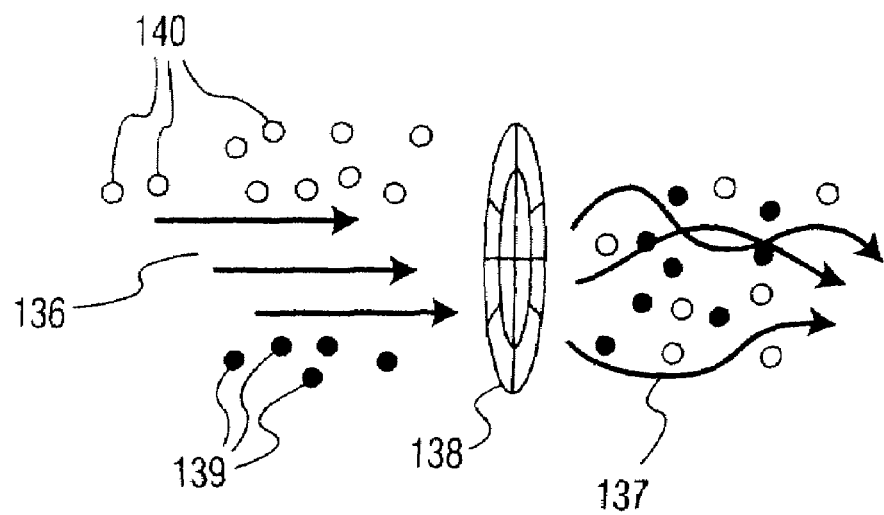
FIG. 11 is a view of a device upstream from an MOE device for inducing turbulence in the fluid flow to homogenize the fluid.

FIG. 11 shows laminar flow 136 in a pipe transformed to turbulent flow 137 by a constriction or an obstruction 138 in the flow path forming a turbulence generator. The circle dots vs the solid dots represent various phases, such as the solid dots 139 represent solid matter and the circle dots 140 represent gas.

In FIG. 2, the dashed region 141 represents turbulent generators. In FIG. 2a, a turbulent generator may comprise a plate 142 with through holes 143 of the same or different sizes. The dashed region 144 represents slits in the plate 142 and the dashed region 145 represents a hole in the plate 142 forming a reduced diameter constriction. In the alternative, in FIG. 2b, pipe 50' has an annular array of radially inwardly directed vanes 146 welded or otherwise attached to the pipe 50' core. The size, placement and orientation of the vanes 146 for generating the desired turbulence can be determined empirically by one of ordinary skill in this art.

Another way to obtain homogeneous sampling is to provide multiple sampling points and average the results. This requires multiple sensors (analyzer devices) in close proximity for analyzing the same property.

Internal Standard for Online Calibration

Over time most sensor devices (MOE devices) change their response both in an oscillatory fashion and in a linear fashion. This change in response is called instrument drift. Instrument drift is caused by a physical change in the components comprising the sensor device. This change can affect electronic as well as optical components. A detector response can for instance change as a function of wavelength. Likewise the attenuation across optical elements can change over time by solid state migration and crystal changes induced by temperature. Optical components can become misaligned. Electronic resistance in wires transistors, and resisters can change. Careful selection of components can mitigate most of these changes, however, these changes are never fully eliminated. This is one reason that instrument calibration must be performed regularly even when the sample matrix is constant.

Two common types of calibrations are external standard calibrations and internal standard calibrations. External standard calibrations are performed with a set of samples for which the components are known. The response of the instrument is then correlated to the properties of the known standards. A mathematical transformation is then applied to the instrument response to derive the properties of unknown samples. For the present embodiments, the MOE performs this mathematical transformation and is the device by which the regression (application of a calibration to unknown samples) is performed.

The regression amounts to multiplication of the sample spectra as a matrix with another matrix often called the loadings matrix or loadings spectra. Because this regression is performed by the MOE, it is impossible to recalibrate a single MOE and it is impossible to perform an external calibration. In addition, it would be difficult to perform an external calibration since the whole device will generally be inaccessible. An internal standard calibration, however, can be provided to adjust the resultant instrument response after the regression is performed.

One method of an internal standard calibration is standard addition (for single components) or generalized standard addition (GSAM) (for multiple interfering components) where standards are added directly to an unknown sample. The response of the sample with a standard addition is compared to the response of the samples without standard addition and instrument drift is determined and corrected. Although this method of internal standard correction may not be feasible for an instrument located in an inaccessible area, a slight alteration of this technique is believed possible.

If an MOE device were to contain multiple standards within the device, then the light may be diverted from the IRE into those samples. One such arrangement, FIG. 11a, wherein parts with the same reference numerals as in FIGS. 2 and 2c represent the same parts, employs a pair of telecommunications optical switches 147 and fiber optic cables 148 to rout the light through internal standards 149 and then through the MOE 80 to the detector 82.

The responses of the internal standards 149 are used to adjust the response of the regression that the MOE 80 provides to the computer altered by the standard. The computer determines the property based on use of the standard. The internal standards 149 need not be comprised of the same material as the samples, but need only to have similar optical responses. They could for instance contain plastic or glass rods doped with dyes to mimic the optical response of the crude petroleum. So long as the internal standards contain the span of optical responses with which the original calibration was performed, then correction is believed possible. Additionally, as in the GSAM, as many internal standards may be necessary as there are interfering (including matrix) factors as was determined in the original calibration. These responses are determined from the original calibration. This method assumes that the internal standards themselves are not affected by drift.

Use of Indicators to Increase Optical Activity

Not all chemical or physical properties can be correlated to optical interaction. For instance pH (a measure of the concentration of hydronium ion in water) is not specifically optically active. The concentration of many of these physical and chemical properties may induce an optical change in a secondary material. These secondary materials are called indicators. For instance the addition of methylene blue to an optically inactive water sample allows pH to be optically measured. Many chemical species that are optically inactive in convenient spectroscopic regions can be measured indirectly through the use of an indicator. Coulimetric spectroscopy is the term for this type of spectroscopy.

Historically the indicator has been added directly to the sample to be measured. A down hole experiment was performed by another party where pH was determined using conventional filters and a pH indicator was introduced into the flow stream ahead of an optical sensor. Recently sensor manufactures are increasingly binding indicators to optical probes so that the same indicator (that bonded to the probe) can be utilized over long periods of time. Ocean Optics for instance manufactures a pH probe based on this principal. Indicators deployed by either method are chosen based on their response to the chemical or physical change of interest as well as the long term durability in the environment of use.

In the event that it is possible to bind an indicator directly to the sample side of the IRE, it may be necessary to protect the indicator from abrasion by removal of the abrasive cleaner, and the addition of a durable semipermeable membrane. Semipermeable membranes allow flow or diffusion across the membrane barrier for certain components. In the case that a physical property such as pressure or temperature was desired to be measured by an indicator, a very durable protective layer could be added since temperature and pressure are transmitted through most materials.

Figure 11A:
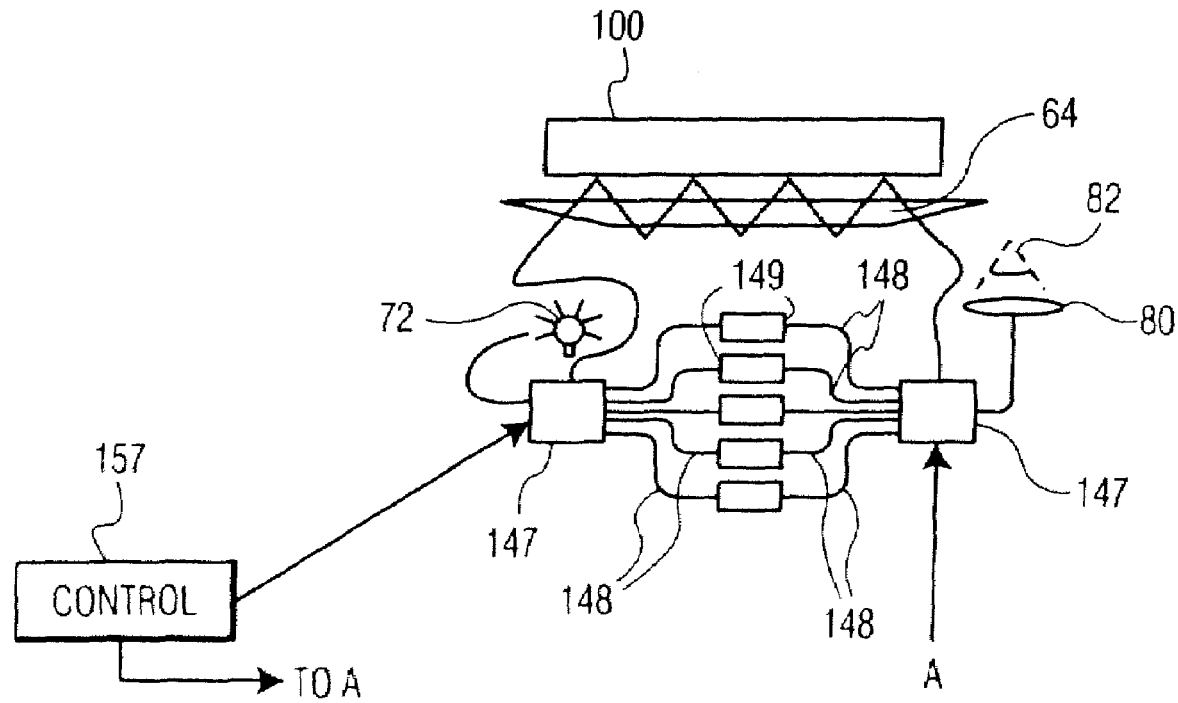
FIG. 11a is a schematic diagram illustrating an internal calibration arrangement for online periodic drift correction of the optical analysis device.
Figure 12:
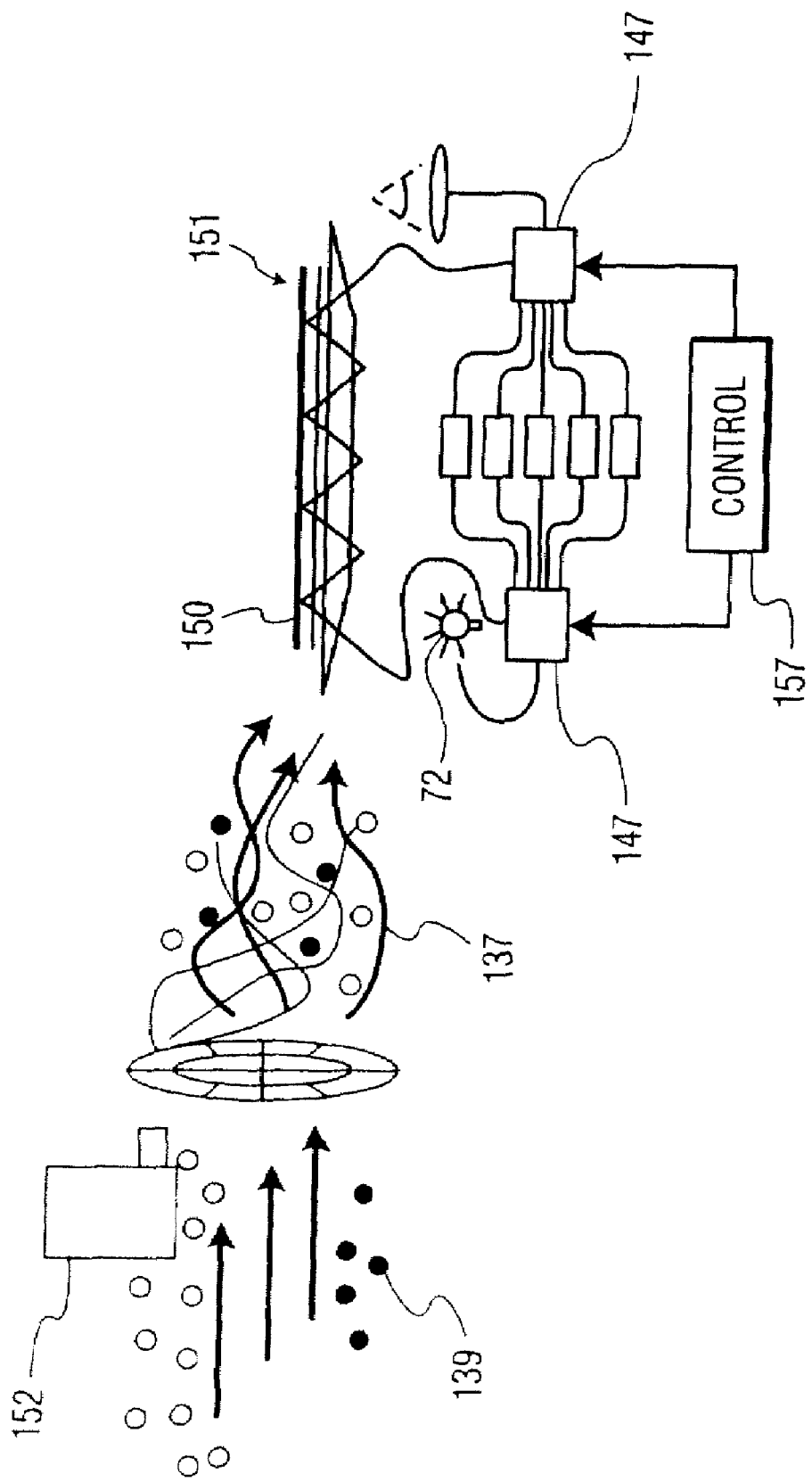
FIG. 12 is a diagram illustrating the use of an indicator for increasing optical interaction.

FIG. 12 shows a bound indicator 150, a membrane or barrier 151 and an upstream indicator 152. The rest of this figure is the same as in FIG. 11a it being understood that the turbine 100, FIG. 11a, is not used in the embodiment of FIG. 12. It is believed that only one method, a bound indicator or upstream indicator, would be used in any given situation. Note that abrasive cleaning as shown in FIG. 11a, could be performed with the use of an upstream indicator 152. Multiple indicators may be added or bound to the IRE or window for multiple properties.

Use of Bellows and a Pressure Balancing Optically Transparent Fluid

In petroleum field applications, normal pressures within pipelines may range from 5,000 psi to 30,000 psi. It could be difficult and expensive to design a pressure housing such as housing 58, FIG. 2, for the IRE-MOE device to withstand these pressures. Therefore it may be useful to fill the inside of the housing such as housing 58 with a fluid designed to balance the internal pressure with that of the external pressure. If an open optical path were to be used within the device then an optically transparent fluid is used. If there is no open path (fiber optics make all optical connections) then this requirement may be relaxed. Still the fluid would have to be non-reactive and non-electrically conductive. One such fluid that may meet all three requirements is silicone oil.

In FIG. 13, in addition, it may be useful to add bellows 153 to the device of FIG. 12 in the housing 58' such as housing 58. The rest of the device may be the same as shown in FIG. 12. The bellows 153 serves as a pressure balancing barrier between the inside and outside of the housing 58'. Bellows are devices that expand and contract with very little resistance. With these improvements to the housing 58' the internal pressure of the housing is believed to be equal to the external pressure and the pressure differential should be zero. Therefore no stress due to pressure will be placed on any of the housing seals (not shown) or the IRE window.

FIG. 13 shows the bound indicator example with the fluid filled housing and the bellows. The method of encasement could just as easily be applied to the upstream indicator embodiment of FIG. 12 or the abrasive cleaning embodiment of FIG. 11a.

Use of Multiple Optical Elements to Track Uncalibrated Components

An advantage of multivariate calibrations is that they can be used to mitigate interferences and sample matrix effects. In fact with the complexity of petroleum systems simple spectroscopic calibrations provide valid results in a few special cases. Another advantage of some multivariate calibrations are that the concentrations of the interference or cause of the matrix effect never need be known. To perform a matrix independent/interference free calibration, only the independent matrices and independent interferences in the samples need to be used for calibration. The regression will fail if an uncalibrated component (matrix or interference) appears in a sample.

Mathematical multivariate regressions have a statistical parameter called the residual of the regression that can be used to determine if an unknown component is adversely affecting results. Due to the nature of the MOE calibration this parameter is not directly available. One property of multivariate calibrations are that many different calibrations may be degenerate. That is two different loadings matrices may yield essentially equivalent results. These loadings spectra use different combinations of the spectroscopic region of interest to arrive at the same result.

An example is acetone in water. Assume that acetone responds at two wavelengths 300 nm and 310 nm. Also assume that both peaks are essentially of equal height. Also assume that the absorptivity coefficient (the calibration parameter that relates optical response to concentration) is 0.1 in both cases with units such that a 10% optical absorption is equivalent to a 1 part per million (ppm) concentration of acetone. A simple loadings matrix may be considered as [0.1] in which 0 is multiplied by the absorption at 300 nm and 0.1 multiplied by the absorption at 310 nm and both products are summed (0+1) to equal 1 ppm.

Alternatively a second loadings matrix could just as equivalently be considered as [0.10]. In this case (1+0)=1 and the answer is the same. [0.05 0.05] yielding (0.5+0.5=1) would be equally valid. In fact, the loadings matrix can be rotated to any infinite number of combinations such that result is the same. In real calibrations, with many hundreds of wavelengths used, interferences, matrix effects, noise, and where peaks are not of the same intensity or stability, there is often an optimal calibration loadings matrix. There can be a few near optimal combinations that are very different from the optimal loadings matrix. In fact MOE construction rarely, if ever, uses the optimal loadings matrix and usually uses a near optimal equivalent that is easier to build.

For two different loadings matrices, it would be extremely unlikely that an uncalibrated component responded identically to both. For instance, assume that in a 1 ppm solution of acetone in water there is 1 ppm of a different ketone that responds at both 300 nm and 310 nm. Assume that the absorption at 300 nm is 10% and the response at 310 nm is 20%. Then the total response at 300 nm would be 20% (10 due to acetone and 10 due to the ketone). In a similar way 310 nm the total response would be 30%. An MOE with the loading spectra of [0.1] would calculate 3 ppm of acetone, but the second with the loading spectra of [0.10] would calculate 2 ppm. Simply since the two numbers are in disagreement, it can be concluded that there is an unknown component affecting results.

However, with knowledge of the loading spectra of the elements, which wavelengths are affected can be determined. Multiple elements would be used to obtain more information. FIG. 14 shows the example from FIG. 13 with two MOE's 154 and two corresponding detectors 155. The use of multiple MOE's can be used with any setup.

It should be understood that the disclosed embodiments are given by way of example and not limitation. One of ordinary skill may make modifications to the disclosed embodiments. It is intended that the invention be defined by the appended claims.

What is claimed is:

1. A method for determining at least one property of a moving stream of fluid in a subsurface well comprising:
   directing light to interact with the moving stream of fluid in the subsurface well, and causing the fluid to produce interacted light from the directed light;
   performing a regression calculation on the interacted light with an optical calculation device responsive to the interacted light incident thereon to produce at least one output light signal manifesting the calculation and the corresponding at least one property; and
   determining the at least one property from the at least one output light signal.

2. The method of claim 1 wherein the step of performing the regression calculation includes generating first and second signals representing respective transmitted and reflected light from the optical calculation device and wherein said determining step includes processing the first and second signals.

3. The method of claim 2 wherein the step of performing the regression analysis comprises applying the interacted light from the fluid to a plurality of stacked optical layers.

4. The method of claim 3 wherein the at least one property is selected from the group consisting essentially of asphaltene, saturates, resins, aromatics, solid particulate content, hydrocarbon composition and content, gas composition C1-C6 and content, $CO_2$, $H_2S$ and correlated PVT properties including GOR, bubble point, density, a formation factor, viscosity, a gas component of a gas phase of petroleum, total stream percentage of water, gas, oil, solid particles, solid types, oil finger printing, reservoir continuity, oil type, and water elements, and wherein the water elements consist essentially of ion composition and content, anions, cations, salinity, organics, Ph, mixing ratios, tracer components, and contamination.

5. The method of claim 1 wherein the causing and performing steps are performed on the fluid flowing through a conduit in the well wherein the flowing fluid has a conduit fluid interface surface, and further including repetitively and continuously reflecting light originating from a source onto the interface surface to produce said interacted light.

6. The method of claim 5, further including the step of generating spectroscopic data from the interacted light with a conventional spectroscopic instrument and then using that generated spectroscopic data for producing said optical calculation device.

7. The method of claim 5, further including the step of providing turbulence to the fluid upstream of said interface surface to provide homogeneous distribution of different components in the fluid receiving said reflected light.

8. The method of claim 5, wherein the fluid comprises crude petroleum, and wherein the method further includes the step of mechanically cleaning deposits from the crude petroleum on the conduit at the fluid interface surface.

9. The method of claim 1 wherein the performing step includes applying the interacted light to a plurality of stacked optical layers forming a multivariate optical calculation device.

10. The method of claim 9, further including the step of providing a plurality of said multivariate optical calculation devices and applying the interacted light to each said device, each device corresponding to a different property to be determined.

11. A method for determining at least one property of crude petroleum flowing in a moving stream in a pipe system comprising:
   directing light to interact with the moving stream of crude petroleum, and causing the petroleum to produce interacted light from the directed light;
   performing a regression calculation on the interacted light with an optical calculation device responsive to the interacted light incident thereon to produce at least one output light signal manifesting the calculation and the corresponding at least one property; and
   determining the at least one property from the at least one output light signal; and
   wherein the directing light step includes applying the light to an internal reflectance element and then repetitively interacting the light with the petroleum with the internal reflectance element to provide multiple interactions for producing a total penetration of light into the petroleum in an amount sufficient to manifest the at least one property.

12. The method of claim 1, further including providing an internal calibration to correct for drift in value of the calculation value and then determining the at least one property according to that corrected drift value.

13. A system for determining at least one property of crude petroleum flowing in a moving stream in a pipe system comprising:
   an apparatus coupled to the pipe system and configured to apply incident light to the flowing petroleum in the pipe system to cause the petroleum to produce interacted light;
   an optical calculation device for performing a regression calculation on the interacted light, the device being responsive to the interacted light incident thereon to produce at least one output light signal manifesting the calculation and the corresponding at least one property; and
   a signal processing arrangement for determining the at least one property from the at least one output light signal.

14. The system of claim 13 wherein the calculation device includes a multivariate optical element that comprises a plurality of optical refraction layers, the layers manifesting a multivariate calculation wherein the result of the calculation correlates with a property of the petroleum.

15. A system for determining at least one property of crude petroleum flowing in a moving stream in a pipe system, comprising:
   an apparatus coupled to the pipe system and configured to apply incident light to the flowing petroleum in the pipe system to cause the petroleum to produce interacted light, wherein the petroleum flowing in the pipe has an interface surface with the pipe, the apparatus comprising,
      a light source for providing the incident light to the petroleum interface surface at one location of the pipe, and
      an internal reflectance element coupled to the pipe at the one location for applying the incident light to the interface surface and then alternatively receiving light from, and reflecting light to the interface surface continuously from the applied incident light to generate the interacted light;
   an optical calculation device for performing a regression calculation on the interacted light, the device being responsive to the interacted light incident thereon to produce at least one output light signal manifesting the calculation and the corresponding at least one property; and
   a signal processing arrangement for determining the at least one property from the at least one output light signal.

16. The system of claim 15, further including a cleaning arrangement for cleaning the surface of the internal reflectance element at the interface surface.

17. The system of claim 13, further including providing an indicator in the petroleum for indicating a parameter of the petroleum.

18. The system of claim 13, further including a housing containing the apparatus and calculation device, the housing including a bellows for compensating for pressure differentials in the housing and in the petroleum.

19. The system of claim 13, further including a turbulence generator in the pipe system upstream from the apparatus.

20. The system of claim 13 wherein the property includes at least one property selected from the group consisting essentially of asphaltene, saturates, resins, aromatics, solid particulate content, $H_2O$ ion-composition and content, hydrocarbon composition and content, gas composition C1-C6 and content, $CO_2$, $H_2S$ and correlated PVT properties including GOR, bubble point, density, an oil formation factor, viscosity, a gas component of a gas phase of the petroleum, total stream percentage of water, gas, oil, solid particles, solid types, oil finger printing, reservoir continuity, oil type, water elements, and wherein the water elements consist essentially of ion composition and content, anions, cations, salinity, organics, pH, mixing ratios, tracer components, and contamination.

21. The system of claim 13, further including at least one turbulence generator in the pipe system for mixing the petroleum upstream relative to the apparatus.

22. The system of claim 21 wherein the at least one turbulent generator comprises at least one of a plurality of vanes or an apertured member, secured to the pipe system for receiving the flowing petroleum.

23. The system of claim 13 wherein the optical calculation device is arranged for generating first and second signals representing respective transmitted and reflected light from the optical calculation device; and wherein the signal processing arrangement is adapted to process the first and second signals to determine the at least one property.

24. The system of claim 13, further including a plurality of said optical calculation devices; and wherein the the interacted light is applied to each said device, each device corresponding to a different property to be determined.

25. The system of claim 13 wherein the apparatus includes an internal reflectance element for repetitively reflecting the light from the petroleum with the internal reflectance element to provide multiple interactions with the petroleum for providing a total light penetration into the petroleum an amount sufficient to manifest the at least one property.

26. The system of claim 13, further including an internal calibration arrangement for correcting for drift in value of the calculation value, the processing arrangement for determining the at least one property according to that corrected drift value.

27. An apparatus for determining a property of a component of crude petroleum flowing in a pipe, comprising:
   a housing having a cavity and arranged to be attached to the pipe, the pipe having an internal region containing the flow of crude petroleum;

a light source in the housing;

an internal reflectance element (IRE) in the housing for transmitting light received from the source via an element input through the element into the attached pipe internal region for applying the light to the petroleum to interact the light with the petroleum and for sequentially receiving the light interacted light at a plurality of element locations, the sequentially received interacted light for being transmitted through an element output;

a multivariate optical filter element (MOE) in the housing for receiving the interacted light transmitted through the element output for performing a regression calculation on the received light and for producing at least one output signal manifesting the regression calculation; and at least one detector in the housing responsive to the at least one output signal for generating a further output signal manifesting said property.

28. The apparatus of claim 27 wherein the internal reflectance element comprises a faceted structure having a first facet forming the input and a second facet forming the output and an interface surface facing the internal region of the pipe.

29. The apparatus of claim 27 wherein the IRE is dimensioned to reflect light from and to the internal region of the pipe a plurality of times, the number of reflections sufficient to enable the system to manifest said property.

30. The apparatus of claim 27 wherein the housing cavity contains a fluid transparent to light.

31. The apparatus of claim 27 further including an expansion bellows coupled to the housing for compensating for pressure differentials between the housing cavity and a region external the housing.

32. The apparatus of claim 27, wherein the pipe comprises a window, and wherein the IRE is attached to the pipe at the window, the pipe for flowing crude petroleum past the window and further comprising:

a connection arrangement for coupling the housing to the window, and a turbulence generator in the pipe upstream from the window.

33. The apparatus of claim 27, further including:

a control mechanism;

at least one internal MOE standard in the housing for calibration of and compensating for drift of the MOE;

a first optical switch in the housing responsive to the control mechanism for selecting and coupling the light from the light source to the at least one internal MOE standard; and a second optical switch responsive to the control for coupling the selected at least one internal MOE standard to the at least one detector.

34. The apparatus of claim 27 further including at least one optically indicator for increasing optical interaction coupled to the IRE for detecting a property of the crude petroleum.

35. The apparatus of claim 34 including a protective membrane for protecting the indicator.

36. The apparatus of claim 32 including a cleaning device for cleaning the window.

37. The apparatus of claim 27 including a plurality of said MOEs and a plurality of said detectors responsive to emissions and transmissions of interacted light from said petroleum.

38. The method of claim 1 further including performing the regression calculation on the interacted light in the subsurface well and determining the at least one property at a location remote from the calculation device by processing the at least one output light signal at the remote location and for generating a further output signal manifesting the determined property at the remote location.

39. The apparatus of claim 13 wherein the crude petroleum is flowing in a pipe, and wherein the signal processing arrangement is located at a location remote from each of the pipe, the optical calculation device and the apparatus for applying incident light.

40. A method for determining at least one property of a moving stream of hydrocarbon-containing fluid in a subsurface well, comprising the steps of:

providing a source of light in the subsurface well and directing the light to interact with the moving stream of hydrocarbon-containing fluid in the subsurface well, and causing the fluid to produce interacted light from the directed light;

performing a regression calculation on the interacted light with an optical calculation device responsive to the interacted light incident thereon to produce at least one output light signal manifesting the calculation and related to the at least one property; and determining the at least one property from the at least one output light signal.

41. The method of claim 40, further comprising the step of causing the fluid to flow through a tool in the subsurface well, and wherein the hydrocarbon-containing fluid flows through a conduit through which the light interacts with the moving stream of fluid.

42. The method of claim 41, wherein the hydrocarbon-containing fluid comprises crude petroleum.

43. An apparatus system to determine a property of a hydrocarbon-containing fluid in a subsurface well, comprising:

a light emitting device configured to apply incident light to a hydrocarbon-containing fluid in a subsurface well to cause the fluid to produce interacted light;

an optical calculation device cooperatively arranged to receive at least a portion of the interacted light that performs a regression calculation on the interacted light, the device responsive to the interacted light incident thereon to produce at least one output light signal manifesting the calculation and related to corresponding property; and a signal processor coupled to receive the at least one output light signal and configured to determine the at least one property from the received output light signal.

44. The apparatus of claim 43, wherein both the apparatus and optical calculation device are located in situ in the subsurface well.

45. The apparatus of claim 13, wherein the pipe system is a down hole pipe located in a well.

46. The apparatus of claim 13, wherein the pipe system is a portion of a pipeline.

47. The apparatus of claim 27, wherein the pipe is a down hole pipe located in a well.

48. The apparatus of claim 27, wherein the pipe is a portion of a pipeline.

* * * * *

UNITED STATES PATENT AND TRADEMARK OFFICE
CERTIFICATE OF CORRECTION

| | | |
|---|---|---|
| PATENT NO. | : 7,697,141 B2 | Page 1 of 1 |
| APPLICATION NO. | : 11/297282 | |
| DATED | : April 13, 2010 | |
| INVENTOR(S) | : Christopher M. Jones et al. | |

It is certified that error appears in the above-identified patent and that said Letters Patent is hereby corrected as shown below:

In column 25, line 65, in Claim 15, delete "to" and insert -- to, --, therefor.

In column 26, line 49, in Claim 24, delete "the the" and insert -- the --, therefor.

Signed and Sealed this

Fourteenth Day of September, 2010

David J. Kappos
*Director of the United States Patent and Trademark Office*